United States Patent
Hopson et al.

(10) Patent No.: US 12,408,914 B2
(45) Date of Patent: Sep. 9, 2025

(54) SYSTEMS AND METHODS FOR CUSTOMIZING MECHANICAL STRENGTH IN STIMULI-RESPONSIVE BIOABSORBABLE MATERIALS

(71) Applicant: CILAG GMBH INTERNATIONAL, Zug (CH)

(72) Inventors: Peyton Hopson, Cincinnati, OH (US); Brody Frost, Fairfield, OH (US); Madelaine Franzoni, Cincinnati, OH (US); Michael J. Vendely, Lebanon, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/484,929

(22) Filed: Oct. 11, 2023

(65) Prior Publication Data
US 2024/0423617 A1    Dec. 26, 2024

Related U.S. Application Data

(60) Provisional application No. 63/522,660, filed on Jun. 22, 2023.

(51) Int. Cl.
*A61B 17/064* (2006.01)
*A61B 17/068* (2006.01)
(Continued)

(52) U.S. Cl.
CPC ........ *A61B 17/0644* (2013.01); *A61B 17/068* (2013.01); *A61B 17/07292* (2013.01);
(Continued)

(58) Field of Classification Search
CPC ..... C08G 63/08; A61L 31/146; A61L 31/148; A61L 27/18; A61L 27/56; A61L 31/06;
(Continued)

(56) References Cited

U.S. PATENT DOCUMENTS 4,264,743 A    4/1981 Maruyama
5,151,315 A    9/1992 Ponnet
(Continued)

FOREIGN PATENT DOCUMENTS

EP    3135323 A1    3/2017
WO    2006060482 A2    6/2006
(Continued)

OTHER PUBLICATIONS

Pattnaik, Ananya, et al. "Designing of Gradient Scaffolds and Their Applications in Tissue Regeneration." Biomaterials, vol. 296, May 1, 2023, p. 122078.
(Continued)

*Primary Examiner* — Nathaniel C Chukwurah
(74) *Attorney, Agent, or Firm* — TROUTMAN PEPPER LOCKE LLP

(57) ABSTRACT

The disclosed technology includes a bioabsorbable material configured to be delivered to tissue. The material includes a shape-memory polymer compressible in a delivery configuration and configured to swell within a predetermined period of time. The shape-memory polymer includes one or more functional groups for reversible bonding between adjacent functional groups to transition between an approximately linear polymer and an approximately non-linear polymer upon exposure to a stimulation.

25 Claims, 9 Drawing Sheets

(51) Int. Cl.
  *A61B 17/072* (2006.01)
  *A61L 17/00* (2006.01)
  *A61L 17/10* (2006.01)
  *A61L 17/14* (2006.01)
  *A61L 31/04* (2006.01)
  *A61L 31/06* (2006.01)
  *A61L 31/10* (2006.01)
  *A61L 31/12* (2006.01)
  *A61L 31/14* (2006.01)
  *A61L 31/16* (2006.01)
  *B29C 65/48* (2006.01)
  *B29C 65/52* (2006.01)
  *C08L 75/04* (2006.01)
  *A61B 17/00* (2006.01)
  *B29L 31/00* (2006.01)

(52) U.S. Cl.
  CPC .............. *A61L 17/005* (2013.01); *A61L 17/10* (2013.01); *A61L 17/145* (2013.01); *A61L 31/041* (2013.01); *A61L 31/06* (2013.01); *A61L 31/10* (2013.01); *A61L 31/128* (2013.01); *A61L 31/129* (2013.01); *A61L 31/146* (2013.01); *A61L 31/148* (2013.01); *A61L 31/16* (2013.01); *B29C 65/4855* (2013.01); *B29C 65/4885* (2013.01); *B29C 65/52* (2013.01); *C08L 75/04* (2013.01); *A61B 2017/00004* (2013.01); *A61B 2017/00526* (2013.01); *A61B 2017/00867* (2013.01); *A61B 2017/00938* (2013.01); *A61B 2017/00951* (2013.01); *A61B 2017/07271* (2013.01); *A61L 2300/604* (2013.01); *A61L 2400/12* (2013.01); *A61L 2420/02* (2013.01); *B29L 2031/7546* (2013.01); *C08L 2203/02* (2013.01); *C08L 2312/00* (2013.01)

(58) Field of Classification Search
  CPC ...... A61L 27/58; C08J 9/26; C08J 9/36; C08J 2207/10; C08J 2201/0482; C08J 2367/04; C08J 2205/02; C08J 2201/048; C08J 2300/16; C08J 2205/05; C08L 67/04
  See application file for complete search history.

(56) References Cited

U.S. PATENT DOCUMENTS

| | | |
|---|---|---|
| 6,325,810 B1 | 12/2001 | Hamilton |
| 8,303,625 B2 * | 11/2012 | Lendlein ............... A61L 17/10 528/80 |
| 8,393,514 B2 | 3/2013 | Shelton, IV et al. |
| 8,496,683 B2 | 7/2013 | Prommersberger |
| 8,657,176 B2 | 2/2014 | Shelton, IV et al. |
| 8,746,535 B2 | 6/2014 | Shelton, IV et al. |
| 8,752,699 B2 | 6/2014 | Morgan et al. |
| 8,777,004 B2 | 7/2014 | Shelton, IV et al. |
| 8,783,542 B2 | 7/2014 | Riestenberg et al. |
| 8,814,025 B2 | 8/2014 | Miller et al. |
| 8,834,522 B2 * | 9/2014 | Lendlein ............... A61L 29/148 528/80 |
| 8,851,354 B2 | 10/2014 | Swensgard et al. |
| 8,857,694 B2 | 10/2014 | Shelton, IV et al. |
| 8,864,009 B2 | 10/2014 | Shelton, IV et al. |
| 8,893,949 B2 | 11/2014 | Shelton, IV et al. |
| 8,899,463 B2 | 12/2014 | Schall et al. |
| 8,925,782 B2 | 1/2015 | Shelton, IV |
| 8,978,956 B2 | 3/2015 | Schall et al. |
| 9,016,542 B2 | 4/2015 | Shelton, IV et al. |
| 9,113,865 B2 | 8/2015 | Shelton, IV et al. |
| 9,168,038 B2 | 10/2015 | Shelton, IV et al. |
| 9,198,662 B2 | 12/2015 | Barton et al. |
| 9,204,880 B2 | 12/2015 | Baxter, III et al. |
| 9,211,120 B2 | 12/2015 | Scheib et al. |
| 9,220,500 B2 | 12/2015 | Swayze et al. |
| 9,220,501 B2 | 12/2015 | Baxter, III et al. |
| 9,272,406 B2 | 3/2016 | Aronhalt et al. |
| 9,295,464 B2 | 3/2016 | Shelton, IV et al. |
| 9,301,753 B2 | 4/2016 | Aldridge et al. |
| 9,301,755 B2 | 4/2016 | Shelton, IV et al. |
| 9,307,987 B2 | 4/2016 | Swensgard et al. |
| 9,307,989 B2 | 4/2016 | Shelton, IV et al. |
| 9,314,247 B2 | 4/2016 | Shelton, IV et al. |
| 9,320,523 B2 | 4/2016 | Shelton, IV et al. |
| 9,332,984 B2 | 5/2016 | Weaner et al. |
| 9,358,005 B2 | 6/2016 | Shelton, IV et al. |
| 9,386,984 B2 | 7/2016 | Aronhalt et al. |
| 9,386,988 B2 | 7/2016 | Baxter, III et al. |
| 9,480,476 B2 | 11/2016 | Aldridge et al. |
| 9,566,061 B2 | 2/2017 | Aronhalt et al. |
| 9,572,574 B2 | 2/2017 | Shelton, IV et al. |
| 9,572,577 B2 | 2/2017 | Lloyd et al. |
| 9,585,657 B2 | 3/2017 | Shelton, IV et al. |
| 9,592,050 B2 | 3/2017 | Schmid et al. |
| 9,629,814 B2 | 4/2017 | Widenhouse et al. |
| 9,693,777 B2 | 7/2017 | Schellin et al. |
| 9,700,317 B2 | 7/2017 | Aronhalt et al. |
| 9,724,098 B2 | 8/2017 | Baxter, III et al. |
| 9,757,124 B2 | 9/2017 | Schellin et al. |
| 9,770,245 B2 | 9/2017 | Swayze et al. |
| 9,775,608 B2 | 10/2017 | Aronhalt et al. |
| 9,788,834 B2 | 10/2017 | Schmid et al. |
| 9,795,383 B2 | 10/2017 | Aldridge et al. |
| 9,795,384 B2 | 10/2017 | Weaner et al. |
| 9,801,634 B2 | 10/2017 | Shelton, IV et al. |
| 9,808,247 B2 | 11/2017 | Shelton, IV et al. |
| 9,826,978 B2 | 11/2017 | Shelton, IV et al. |
| 9,833,236 B2 | 12/2017 | Shelton, IV et al. |
| 9,833,238 B2 | 12/2017 | Baxter, III et al. |
| 9,833,242 B2 | 12/2017 | Baxter, III et al. |
| 9,839,420 B2 | 12/2017 | Shelton, IV et al. |
| 9,839,422 B2 | 12/2017 | Schellin et al. |
| 9,839,423 B2 | 12/2017 | Vendely et al. |
| 9,844,372 B2 | 12/2017 | Shelton, IV et al. |
| 9,844,376 B2 | 12/2017 | Baxter, III et al. |
| 9,848,875 B2 | 12/2017 | Aronhalt et al. |
| 9,861,361 B2 | 1/2018 | Aronhalt et al. |
| 9,883,861 B2 | 2/2018 | Shelton, IV et al. |
| 9,884,456 B2 | 2/2018 | Schellin et al. |
| 9,918,716 B2 | 3/2018 | Baxter, III et al. |
| 9,924,944 B2 | 3/2018 | Shelton, IV et al. |
| 9,924,947 B2 | 3/2018 | Shelton, IV et al. |
| 9,962,161 B2 | 5/2018 | Scheib et al. |
| 9,974,538 B2 | 5/2018 | Baxter, III et al. |
| 10,028,743 B2 | 7/2018 | Shelton, IV et al. |
| 10,052,104 B2 | 8/2018 | Shelton, IV et al. |
| 10,064,624 B2 | 9/2018 | Shelton, IV et al. |
| 10,136,890 B2 | 11/2018 | Shelton, IV et al. |
| 10,149,682 B2 | 12/2018 | Shelton, IV et al. |
| 10,182,819 B2 | 1/2019 | Shelton, IV |
| 10,213,198 B2 | 2/2019 | Aronhalt et al. |
| 10,258,330 B2 | 4/2019 | Shelton, IV et al. |
| 10,258,332 B2 | 4/2019 | Schmid et al. |
| 10,265,072 B2 | 4/2019 | Shelton, IV et al. |
| 10,271,849 B2 | 4/2019 | Vendely et al. |
| 10,285,700 B2 | 5/2019 | Scheib |
| 10,335,148 B2 | 7/2019 | Shelton, IV et al. |
| 10,335,150 B2 | 7/2019 | Shelton, IV |
| 10,390,823 B2 | 8/2019 | Shelton, IV et al. |
| 10,398,436 B2 | 9/2019 | Shelton, IV et al. |
| 10,426,481 B2 | 10/2019 | Aronhalt et al. |
| 10,441,285 B2 | 10/2019 | Shelton, IV et al. |
| 10,588,623 B2 | 3/2020 | Schmid et al. |
| 10,603,039 B2 | 3/2020 | Vendely et al. |
| D882,782 S | 4/2020 | Shelton, IV et al. |
| 10,617,417 B2 | 4/2020 | Baxter, III et al. |
| 10,617,418 B2 | 4/2020 | Barton et al. |
| 10,624,861 B2 | 4/2020 | Widenhouse et al. |
| D885,574 S | 5/2020 | Shelton, IV et al. |
| 10,667,808 B2 | 6/2020 | Baxter, III et al. |
| 10,695,061 B2 | 6/2020 | Vendely et al. |
| 10,743,877 B2 | 8/2020 | Shelton, IV et al. |

(56) References Cited

U.S. PATENT DOCUMENTS

| | | | |
|---|---|---|---|
| 10,779,817 B2 | 9/2020 | Shelton, IV et al. | |
| 10,799,237 B2 | 10/2020 | Shelton, IV et al. | |
| 10,813,637 B2 | 10/2020 | Shelton, IV et al. | |
| 10,835,249 B2 | 11/2020 | Schellin et al. | |
| 10,869,669 B2 | 12/2020 | Shelton, IV et al. | |
| 10,905,418 B2 | 2/2021 | Shelton, IV et al. | |
| 10,952,724 B2 | 3/2021 | Shelton, IV et al. | |
| 10,959,721 B2 | 3/2021 | Shelton, IV et al. | |
| 10,966,713 B2 | 4/2021 | Shelton, IV et al. | |
| 10,980,533 B2 | 4/2021 | Shelton, IV et al. | |
| 10,980,539 B2 | 4/2021 | Harris et al. | |
| D920,513 S | 5/2021 | Shelton, IV et al. | |
| 11,006,950 B2 | 5/2021 | Harris et al. | |
| 11,020,115 B2 | 6/2021 | Scheib et al. | |
| 11,058,425 B2 | 7/2021 | Widenhouse et al. | |
| 11,083,452 B2 | 8/2021 | Schmid et al. | |
| 11,118,025 B2* | 9/2021 | Donners | C08G 63/08 |
| 11,154,296 B2 | 10/2021 | Aronhalt et al. | |
| 11,154,297 B2 | 10/2021 | Swayze et al. | |
| 11,155,946 B2 | 10/2021 | Vendely et al. | |
| 11,185,325 B2 | 11/2021 | Shelton, IV et al. | |
| D940,318 S | 1/2022 | Shelton, IV et al. | |
| 11,291,449 B2 | 4/2022 | Swensgard et al. | |
| 11,337,698 B2 | 5/2022 | Baxter et al. | |
| 11,395,651 B2 | 7/2022 | Shelton, IV et al. | |
| D960,364 S | 8/2022 | Shelton, IV et al. | |
| 11,406,377 B2 | 8/2022 | Schmid et al. | |
| 11,406,378 B2 | 8/2022 | Baxter et al. | |
| 11,446,027 B2 | 9/2022 | Harris et al. | |
| 11,446,032 B2 | 9/2022 | Harris et al. | |
| 11,471,158 B2 | 10/2022 | Harris et al. | |
| 11,504,116 B2 | 11/2022 | Schmid et al. | |
| 11,504,125 B2 | 11/2022 | Shelton, IV et al. | |
| 11,534,168 B2 | 12/2022 | Harris et al. | |
| 11,534,169 B2 | 12/2022 | Harris et al. | |
| 11,540,824 B2 | 1/2023 | Shelton, IV et al. | |
| 11,540,832 B2 | 1/2023 | Harris et al. | |
| 11,540,833 B2 | 1/2023 | Harris et al. | |
| 11,553,915 B2 | 1/2023 | Harris et al. | |
| 11,559,496 B2 | 1/2023 | Widenhouse et al. | |
| 11,571,215 B2 | 2/2023 | Shelton, IV et al. | |
| 11,583,277 B2 | 2/2023 | Shelton, IV et al. | |
| 11,602,340 B2 | 3/2023 | Schmid et al. | |
| 11,602,341 B2 | 3/2023 | Shelton, IV et al. | |
| 11,612,396 B2 | 3/2023 | Harris et al. | |
| 11,638,584 B2 | 5/2023 | Harris et al. | |
| 11,642,130 B2 | 5/2023 | Harris et al. | |
| 11,648,007 B2 | 5/2023 | Harris et al. | |
| 11,672,536 B2 | 6/2023 | Shelton, IV et al. | |
| 11,672,537 B2 | 6/2023 | Harris et al. | |
| 11,678,883 B2 | 6/2023 | Harris et al. | |
| 11,684,360 B2 | 6/2023 | Shelton, IV et al. | |
| 11,690,617 B2 | 7/2023 | Harris et al. | |
| 11,701,114 B2 | 7/2023 | Shelton, IV et al. | |
| 11,707,279 B2 | 7/2023 | Harris et al. | |
| 11,737,754 B2 | 8/2023 | Shelton, IV et al. | |
| 11,793,509 B2 | 10/2023 | Baxter, III et al. | |
| 11,812,965 B2 | 11/2023 | Baxter, III et al. | |
| 11,839,374 B2 | 12/2023 | Shelton, IV et al. | |
| 11,849,950 B2 | 12/2023 | Shelton, IV et al. | |
| 11,849,952 B2 | 12/2023 | Shelton, IV | |
| 11,850,310 B2 | 12/2023 | Shelton, IV et al. | |
| D1,013,171 S | 1/2024 | Shelton, IV et al. | |
| 11,864,765 B2 | 1/2024 | Shelton, IV et al. | |
| 11,896,226 B2 | 2/2024 | Shelton, IV et al. | |
| 11,911,027 B2 | 2/2024 | Aronhalt et al. | |
| 11,918,210 B2 | 3/2024 | Shelton, IV et al. | |
| 11,925,354 B2 | 3/2024 | Shelton, IV et al. | |
| 11,957,795 B2 | 4/2024 | Schmid et al. | |
| 2005/0113510 A1 | 5/2005 | Feldstein | |
| 2009/0090763 A1 | 4/2009 | Zemlok et al. | |
| 2010/0116868 A1 | 5/2010 | Prommersberger | |
| 2012/0080336 A1 | 4/2012 | Shelton, IV et al. | |
| 2012/0080344 A1 | 4/2012 | Shelton, IV | |
| 2012/0080478 A1 | 4/2012 | Morgan et al. | |
| 2012/0080498 A1 | 4/2012 | Shelton, IV et al. | |
| 2013/0153641 A1 | 6/2013 | Shelton, IV et al. | |
| 2013/0211520 A1 | 8/2013 | Hoganson | |
| 2013/0234372 A1 | 9/2013 | Almutairi | |
| 2013/0256374 A1 | 10/2013 | Shelton, IV | |
| 2013/0256375 A1 | 10/2013 | Shelton, IV | |
| 2013/0256380 A1 | 10/2013 | Schmid et al. | |
| 2014/0166726 A1 | 6/2014 | Schellin | |
| 2014/0291379 A1 | 10/2014 | Schellin et al. | |
| 2015/0217028 A1 | 8/2015 | Pacetti | |
| 2015/0282810 A1 | 10/2015 | Shelton, IV | |
| 2015/0313594 A1 | 11/2015 | Shelton, IV et al. | |
| 2015/0351753 A1 | 12/2015 | Shelton, IV | |
| 2016/0074040 A1 | 3/2016 | Widenhouse et al. | |
| 2016/0183944 A1 | 6/2016 | Swensgard et al. | |
| 2016/0199063 A1 | 7/2016 | Mandakolathur Vasudevan et al. | |
| 2017/0049448 A1 | 2/2017 | Widenhouse | |
| 2017/0055986 A1 | 3/2017 | Harris | |
| 2017/0232157 A1 | 8/2017 | Rege | |
| 2018/0116658 A1 | 5/2018 | Aronhalt, IV et al. | |
| 2018/0140299 A1 | 5/2018 | Weaner et al. | |
| 2018/0235626 A1 | 8/2018 | Shelton, IV | |
| 2018/0250434 A1 | 9/2018 | Ker | |
| 2019/0059889 A1 | 2/2019 | Shelton, IV et al. | |
| 2019/0090871 A1 | 3/2019 | Shelton, IV et al. | |
| 2019/0133578 A1 | 5/2019 | Kriksunov et al. | |
| 2019/0254667 A1 | 8/2019 | Vendely et al. | |
| 2019/0254668 A1 | 8/2019 | Vendely et al. | |
| 2019/0254669 A1 | 8/2019 | Shelton, IV et al. | |
| 2019/0269400 A1 | 9/2019 | Mandakolathur Vasudevan et al. | |
| 2020/0085435 A1 | 3/2020 | Shelton, IV et al. | |
| 2020/0187943 A1 | 6/2020 | Shelton, IV et al. | |
| 2020/0376158 A1 | 12/2020 | Moore | |
| 2021/0059661 A1 | 3/2021 | Schmid et al. | |
| 2021/0077107 A1 | 3/2021 | Harris | |
| 2021/0085315 A1 | 3/2021 | Aronhalt et al. | |
| 2021/0259681 A1 | 8/2021 | Shelton, IV et al. | |
| 2021/0259986 A1 | 8/2021 | Widenhouse et al. | |
| 2021/0267589 A1 | 9/2021 | Swayze et al. | |
| 2021/0282767 A1 | 9/2021 | Shelton, IV et al. | |
| 2021/0290226 A1 | 9/2021 | Mandakolathur Vasudevan et al. | |
| 2022/0000481 A1* | 1/2022 | Sung | A61L 27/507 |
| 2022/0151611 A1 | 5/2022 | Shelton, IV et al. | |
| 2022/0167970 A1 | 6/2022 | Aronhalt et al. | |
| 2022/0175370 A1 | 6/2022 | Shelton, IV et al. | |
| 2022/0175372 A1 | 6/2022 | Shelton, IV et al. | |
| 2022/0211367 A1 | 7/2022 | Schmid et al. | |
| 2022/0218348 A1 | 7/2022 | Swensgard et al. | |
| 2022/0313145 A1 | 10/2022 | Shelton, IV et al. | |
| 2022/0313245 A1 | 10/2022 | Shelton, IV et al. | |
| 2022/0313248 A1 | 10/2022 | Shelton, IV et al. | |
| 2022/0313253 A1 | 10/2022 | Shelton, IV et al. | |
| 2022/0313255 A1 | 10/2022 | Shelton, IV et al. | |
| 2022/0313256 A1 | 10/2022 | Shelton, IV et al. | |
| 2022/0313259 A1 | 10/2022 | Shelton, IV et al. | |
| 2022/0313262 A1 | 10/2022 | Shelton, IV et al. | |
| 2022/0338870 A1 | 10/2022 | Swayze et al. | |
| 2022/0354495 A1 | 11/2022 | Baxter, III et al. | |
| 2022/0370684 A1 | 11/2022 | Nseir Manassa | |
| 2023/0140285 A1 | 5/2023 | Boudreaux | |
| 2023/0210525 A1 | 7/2023 | Shelton, IV et al. | |
| 2023/0301656 A1 | 9/2023 | Seow | |
| 2023/0301657 A1 | 9/2023 | Zeiner et al. | |
| 2023/0301674 A1 | 9/2023 | Rector et al. | |
| 2023/0301675 A1 | 9/2023 | Seow et al. | |
| 2023/0320742 A1 | 10/2023 | Bakos et al. | |

FOREIGN PATENT DOCUMENTS

| | | |
|---|---|---|
| WO | 2009020797 A2 | 2/2009 |
| WO | 2014004205 A1 | 1/2014 |
| WO | 2014004208 A1 | 1/2014 |
| WO | 2015095755 A1 | 6/2015 |
| WO | 2015191219 A1 | 12/2015 |
| WO | 2016153903 A2 | 9/2016 |

(56) References Cited

FOREIGN PATENT DOCUMENTS

WO  2017040189 A1  3/2017
WO  2018229574 A1  12/2018

OTHER PUBLICATIONS

Mi, Hao-Yang, et al. "In Situ Synthesis of Polyurethane Scaffolds with Tunable Properties by Controlled Crosslinking of Tri-Block Copolymer and Polycaprolactone Trio I for Tissue Regeneration." Chemical Engineering Journal, vol. 348, Sep. 1, 2018, pp. 786-798.
Ulery, Brett D. "Biomedical Applications of Biodegradable Polymers." Journal of Polymer Science Part B: Polymer Physics, vol. 49, No. 12, Jun. 15, 2011, pp. 832-864. Published Jun. 12, 2012 (Jun. 12, 2012).
Kaikade, Dhiraj S., et al. "Polyurethane Foams from Vegetable Oil-Based Polyols: A Review." Polymer Bulletin, vol. 80, No. 3, Mar. 11, 2022, pp. 2239-2261.
Habault, Damien, et al. "Light-Triggered Self-Healing and Shape-Memory Polymers." Chemical Society Reviews, vol. 42, No. 17, Jan. 1, 2013, p. 7244.
Peng, Ke, et al. "Light Manipulation for Fabrication of Hydrogels and Their Biological Applications." Acta Biomaterialia, Elsevier, Amsterdam, NL, vol. 137, Oct. 9, 2021, pp. 20-43.
International Search Authority, "International Search Report and Written Opinion of the International Searching Authority," for related PCT Application No. PCT/IB2024/055986, dated Sep. 10, 2024.

* cited by examiner

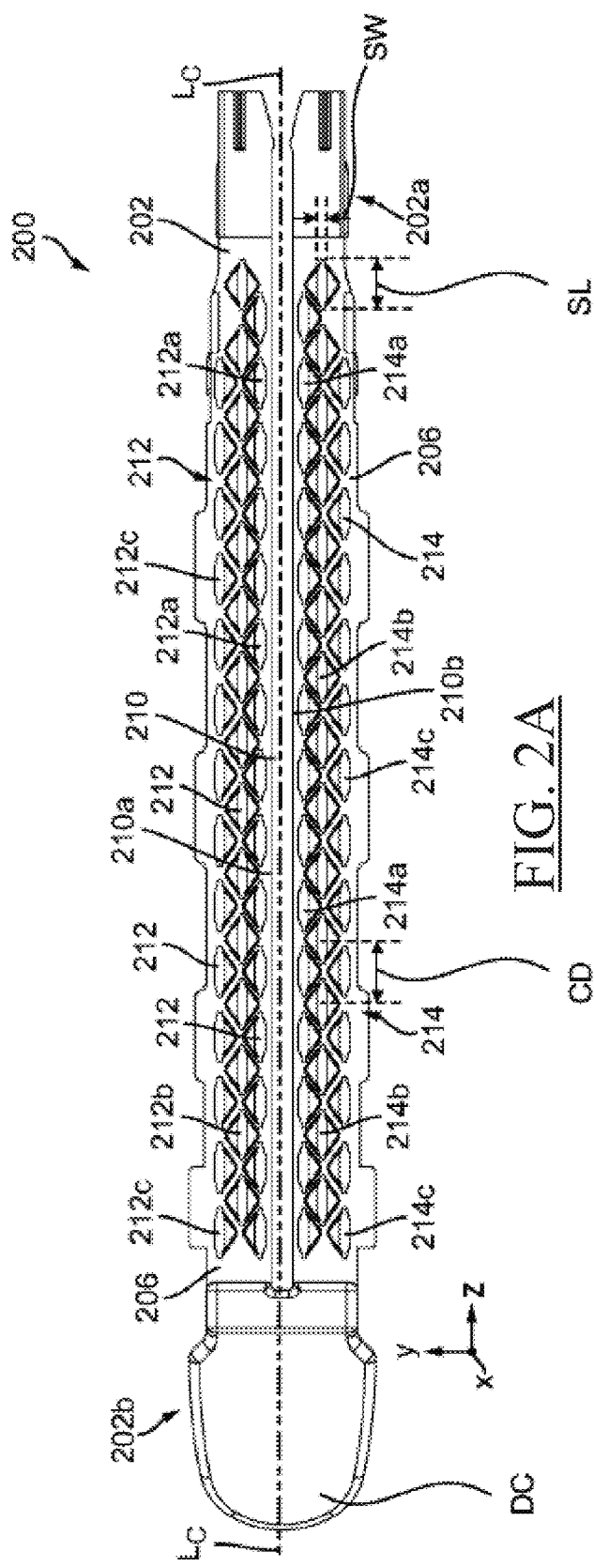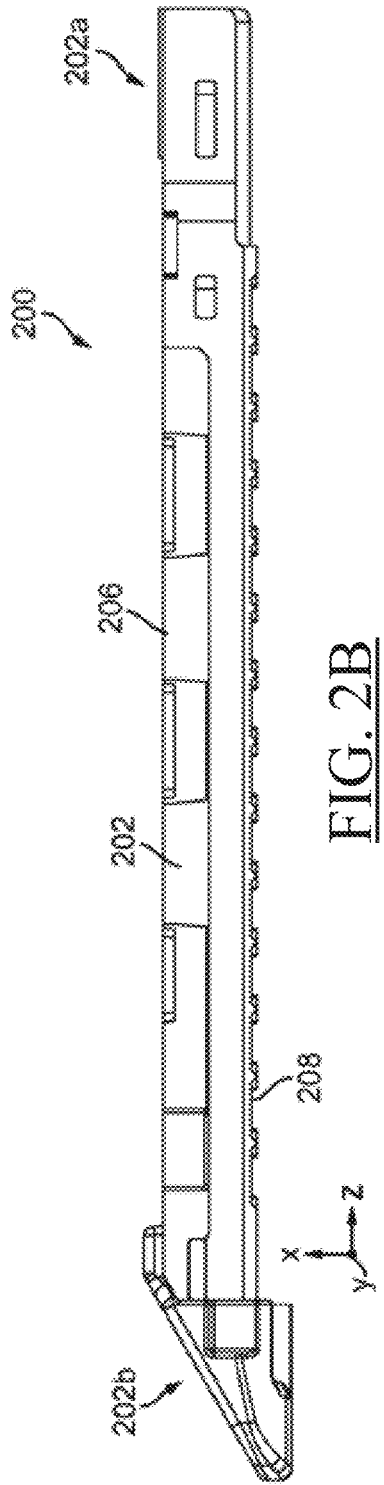
FIG. 2A
FIG. 2B

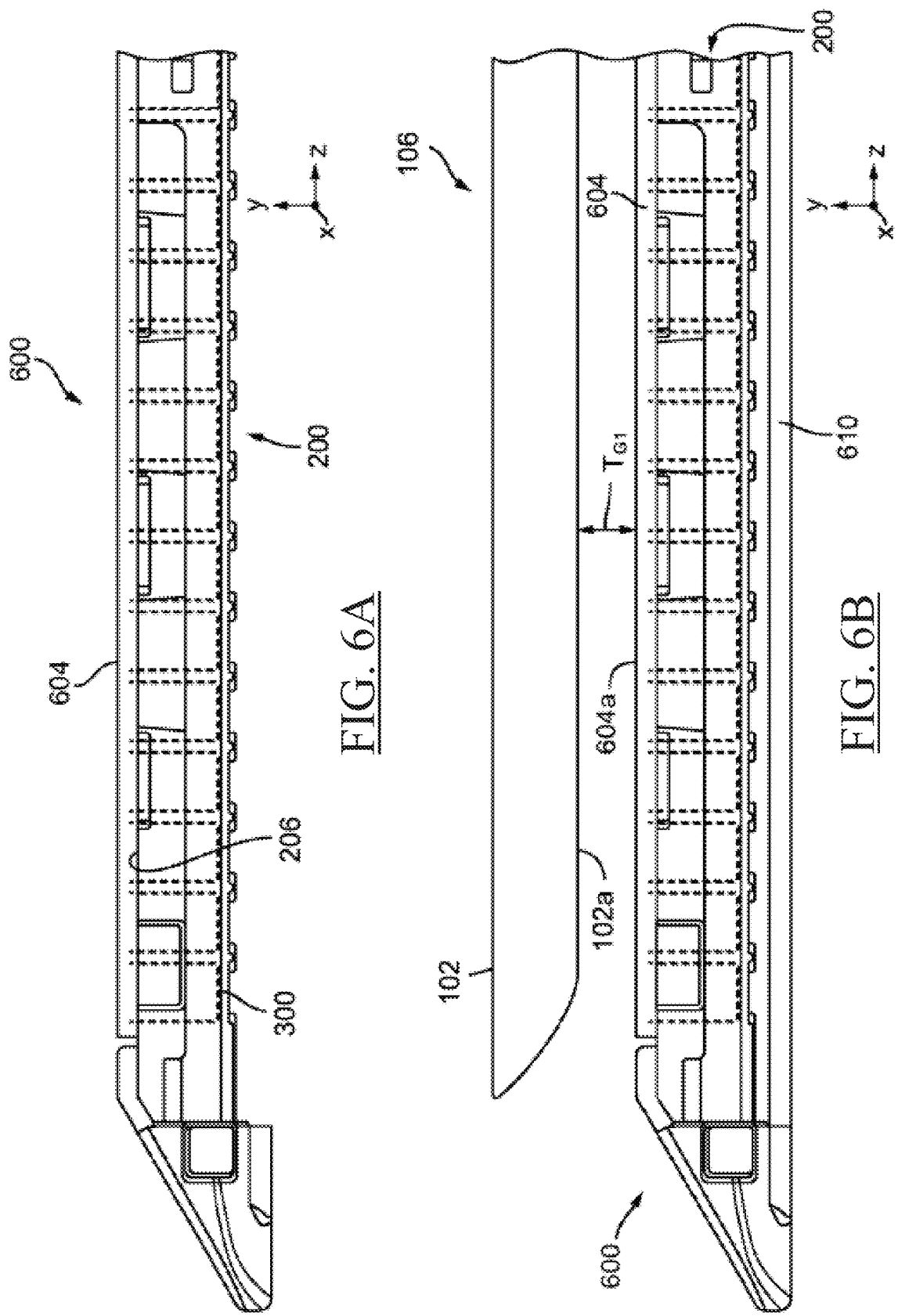

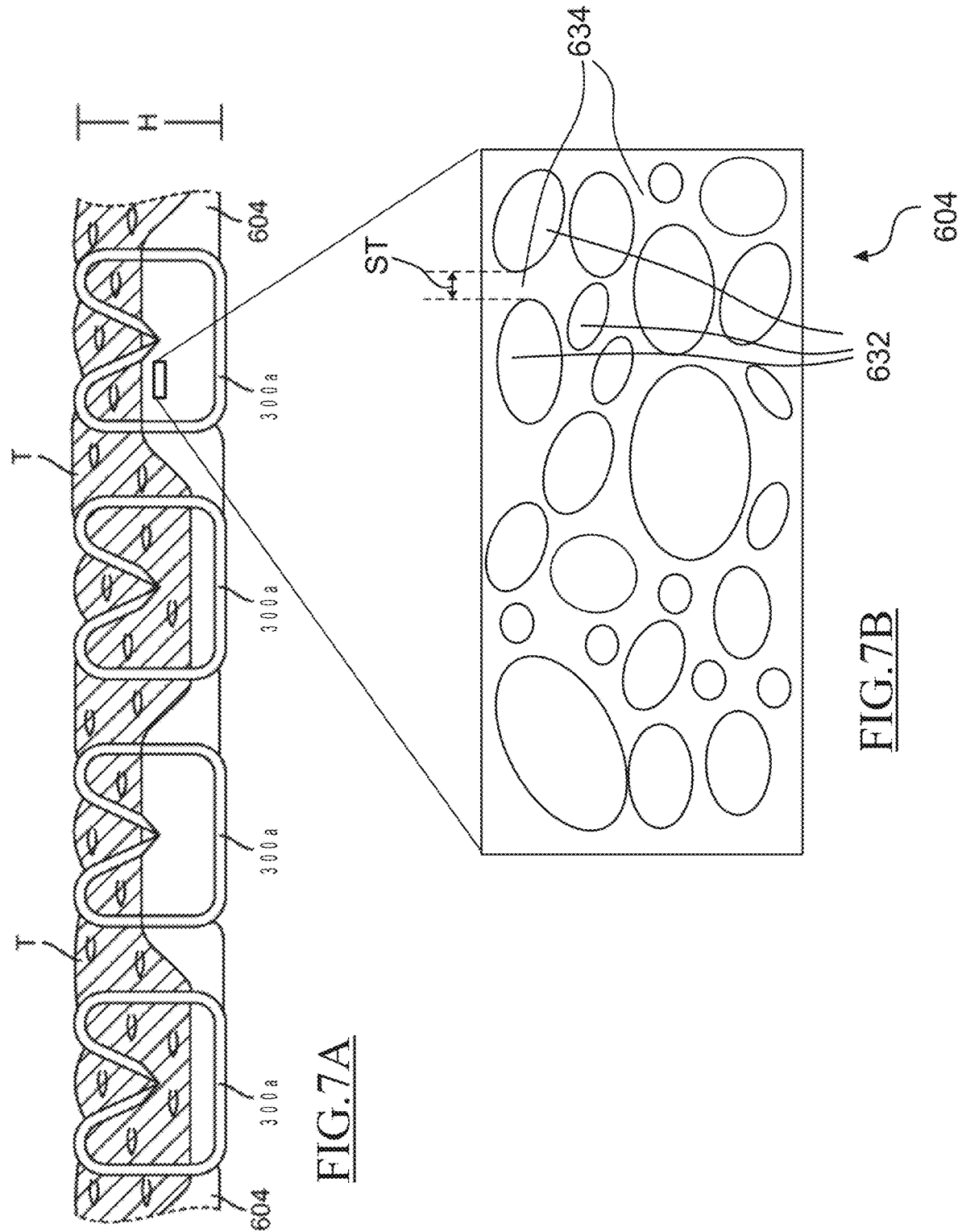

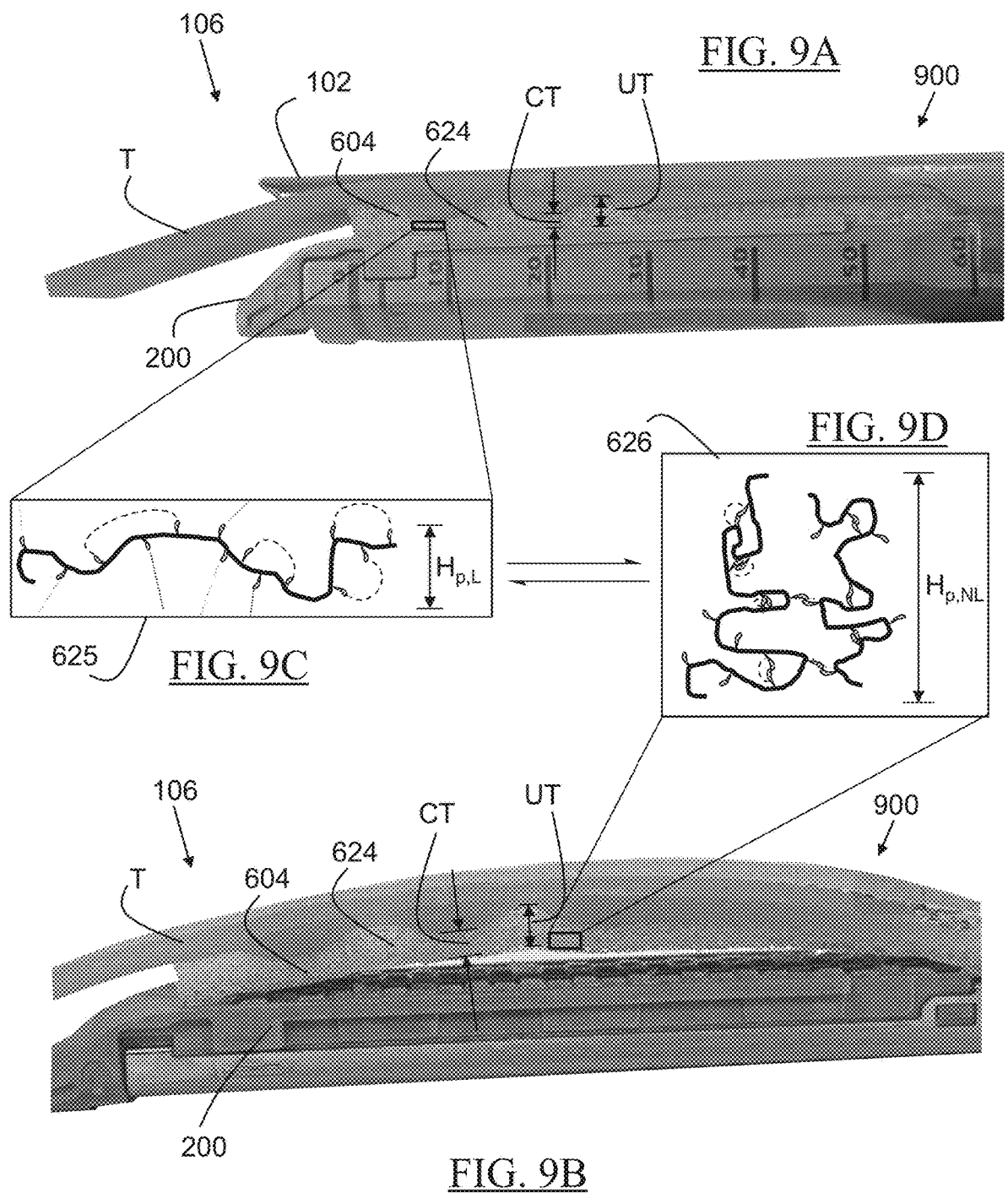

SYSTEMS AND METHODS FOR CUSTOMIZING MECHANICAL STRENGTH IN STIMULI-RESPONSIVE BIOABSORBABLE MATERIALS

CROSS-REFERENCE TO RELATED APPLICATIONS

This application claims priority under 35 U.S.C. § 119 to U.S. Provisional Patent Application No. 63/522,660, filed Jun. 22, 2023, the entire contents of which are fully incorporated herein by reference.

FIELD

The present invention relates generally to systems and methods for customizing mechanical properties via stimuli-responsive functional groups in bioabsorbable materials.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle (some of which are directly user operable, others of which are operable by a user via a robotic interface) with an elongate shaft extending from the handle and having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed, and the device is actuated. Some staplers include a knife configured to travel between rows of staples in the staple cartridge to longitudinally cut and/or open the stapled tissue between the stapled rows.

SUMMARY

There is provided, in accordance with an example of the present invention, a bioabsorbable material configured to be delivered to tissue. The material includes a shape-memory polymer compressible in a delivery configuration and configured to swell within a predetermined period of time. The shape-memory polymer includes one or more functional groups for reversible bonding between adjacent functional groups to transition between an approximately linear polymer and an approximately non-linear polymer upon exposure to a stimulation.

There is provided, in accordance with an exemplary embodiment of the present invention, a shape-memory polymer compressible in a delivery configuration and configured to swell within a predetermined period of time upon exposure to a stimulation. The shape-memory polymer can include a polyurethane backbone and one or more functional groups for reversible bonding between adjacent functional groups to transition between an approximately linear polymer to an approximately non-linear polymer.

There is provided, in accordance with an example of the present invention, a method to form a bioabsorbable material. The method can include the steps of adding, to a polyurethane polymer, a functional group and chemically bonding the polyurethane polymer and functional groups to form a shape-memory polymer. The functional group can include at least one of a diene and a dienophile moiety, a styrylpyrene moiety, an azo moiety, an ortho-nitrobenzyl moiety, a coumarin moiety, an anthracene moiety, a disulfide moiety, a diselenide moiety, or combinations thereof.

BRIEF DESCRIPTION OF THE DRAWINGS

This invention will be more fully understood from the following detailed description taken in conjunction with the accompanying drawings, in which:

FIG. 2A is a top view of a staple cartridge for use with the surgical stapling and severing instrument of FIG. 1;

FIG. 2B is a side view of the staple cartridge of FIG. 2A;

FIG. 6A is a longitudinal cross-sectional view of an exemplary surgical cartridge assembly having a compressible non-fibrous adjunct attached to a top or deck surface of a staple cartridge;

FIG. 6B is a longitudinal cross-sectional view of a surgical end effector having an anvil pivotably coupled to an elongate channel and the surgical cartridge assembly of FIG. 6A disposed within and coupled to the elongate channel, showing the anvil in a closed position without any tissue between the anvil and the adjunct;

FIG. 7A is a partial-schematic illustrating the adjunct of FIGS. 6A-6B in a tissue deployed condition;

FIG. 7B is a diagram showing an enlarged portion of an exemplary adjunct with a porous structure;

FIG. 9A is a side view of an exemplary end effector having an adjunct of bioabsorbable material in a delivery configuration;

FIG. 9B is a side view of an exemplary end effector having an adjunct of bioabsorbable material after firing and release from cartridge;

FIGS. 9C and 9D illustrate example reversible transformations from linear polymers to complex architectures;

DETAILED DESCRIPTION

Figure 1:
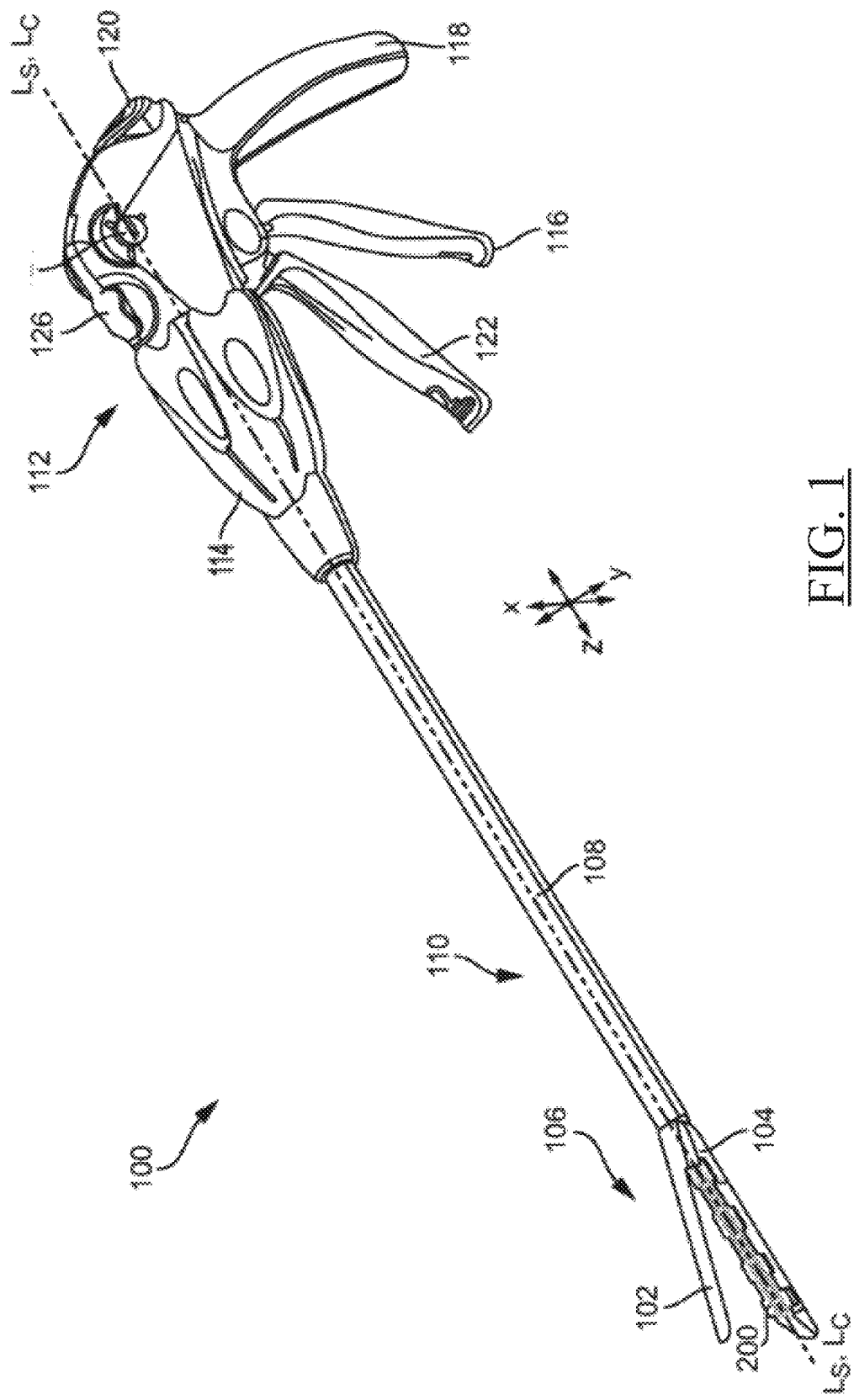
FIG. 1 is a perspective view of one exemplary embodiment of a conventional surgical stapling and severing instrument.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In addition, throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Similarly, as used herein, "substantially free" of something, or "substantially pure", and like characterizations, can include both being "at least substantially free" of something, or "at least substantially pure", and being "completely free" of something, or "completely pure."

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" or "cycloaliphatic"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. Suitable aliphatic groups include, but are not limited to, linear or branched, substituted or unsubstituted alkyl, alkenyl, alkynyl groups and hybrids thereof such as cycloalkyl, (cycloalkyl)alkyl, (cycloalkenyl)alkyl or (cycloalkyl)alkenyl.

The term "alkyl," unless otherwise indicated, as used herein, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, wherein the one or more substituents are independently $C_1$-$C_{10}$ alkyl. In some embodiments, "cycloalkyl" (or "carbocycle") refers to a monocyclic $C_3$-$C_6$ hydrocarbon that is completely saturated or that contains one or more units of unsaturation, but which is not aromatic, that has a single point of attachment to the rest of the molecule. A carbocycle can be, under certain circumstances, a bridged bicyclic or a fused ring such as, e.g., an ortho-fused carbocycle, a spirofused carbocycle, etc. Examples of "alkyl" groups include, but are not limited to, methyl, ethyl, propyl, isopropyl, butyl, iso-butyl, sec-butyl, tert-butyl, pentyl, hexyl, heptyl, cyclopropyl, cyclobutyl, cyclopentyl, cyclohexyl, cycloheptyl, norbornyl, and the like.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkoxy" means an alkyl radical attached through an oxygen linking atom, represented by —O-alkyl. For example, "($C_1$-$C_4$)alkoxy" includes methoxy, ethoxy, propoxy, and butoxy.

The term "aryl," used alone or as part of a larger moiety, refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of compounds described herein, "aryl" refers to an aromatic ring system which includes, but is not limited to, phenyl, naphthyl, anthracyl and the like, which may bear one or more substituents. It will be appreciated that an "aryl" group can comprise carbon and heteroatom ring members.

As described herein, compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

The term "polyurethane," as used herein, refers to a polymeric reaction product of an isocyanate and a polyol, and is not limited to those polymers which include only urethane or polyurethane linkages. It is well understood by those of ordinary skill in the art of preparing polyurethanes that the polyurethane polymers may also include linkages such as allophanate, carbodiimide, and other linkages described herein in addition to urethane linkages.

The expressions "reaction system," "reactive formulation," "reaction product," and "reactive mixture" are interchangeably used herein, and all refer to a combination of reactive compounds used to make the bioabsorbable material according to the disclosure.

The term "room temperature" refers to temperatures of about 20° C., this means referring to temperatures in the range 18° C. to 25° C. Such temperatures will include 18° C., 19° C., 20° C., 21° C., 22° C., 23° C., 24° C. and 25° C.

Unless otherwise expressed, the "weight percentage" (indicated as % wt. or wt. %) of a component in a composition refers to the weight of the component over the total weight of the composition in which it is present and is expressed as percentage.

"Glass transition temperature" and "$T_g$" as referred to herein refers to the temperature at which a reversible transition from a hard glass condition into a rubber-elastic condition occurs.

Surgical stapling assemblies and methods for manufacturing and using the same are provided. In general, a surgical stapling assembly can include a staple cartridge having staples disposed therein and an adjunct configured to be releasably retained on the staple cartridge. As discussed herein, the various adjuncts provided can be configured to compensate for variations in tissue properties, such as variations in tissue thickness, and/or to promote tissue ingrowth when the adjuncts are stapled to tissue. As discussed herein, an adjunct can include a bioabsorbable material, such as a foam.

An exemplary stapling assembly can include a variety of features to facilitate application of a surgical staple, as described herein and illustrated in the drawings. However, a person skilled in the art will appreciate that the stapling assembly can include only some of these features and/or it can include a variety of other features known in the art. The stapling assemblies described herein are merely intended to represent certain exemplary examples. Moreover, while the adjuncts are described in connection with surgical staple cartridge assemblies, the adjuncts can be used in connection with staple reloads that are not cartridge based or any type of surgical instrument.

FIG. 1 illustrates an exemplary surgical stapling and severing device 100 suitable for use with an implantable adjunct. The illustrated surgical stapling and severing device 100 includes end effector 106 having an anvil 102 that is pivotably coupled to an elongate channel 104. As a result, the end effector 106 can move between an open position, as shown in FIG. 1, and a closed position in which the anvil 102 is positioned adjacent to the elongate channel 104 to engage tissue therebetween. The end effector 106 can be attached at its proximal end to an elongate shaft 108 forming an implement portion 110. When the end effector 106 is closed, or at least substantially closed, (e.g., the anvil 102 moves from the open position in FIG. 1 toward the elongate channel) the implement portion 110 can present a sufficiently small cross-section suitable for inserting the end effector 106 through a trocar. While the device 100 is configured to staple and sever tissue, surgical devices configured to staple but not sever tissue are also contemplated herein.

In various instances, the end effector 106 can be manipulated by a handle 112 connected to the elongate shaft 108. The handle 112 can include user controls such as a rotation knob 114 that rotates the elongate shaft 108 and the end effector 106 about a longitudinal axis (Ls) of the elongate shaft 108 and an articulation control 115 that can articulate the end effector 106 about an articulate axis (TA) that is substantially transverse to the longitudinal axis (Ls) of the elongate shaft 108. Further controls include a closure trigger 116 which can pivot relative to a pistol grip 118 to close the end effector 106. A closure release button 120 can be outwardly presented on the handle 112 when the closure trigger 116 is clamped such that the closure release button 120 can be depressed to unclamp the closure trigger 116 and open the end effector 106, for example. Handle 112 may also take the form of an interface for connection to a surgical robot.

In some examples, a firing trigger 122, which can pivot relative to the closure trigger 116, can cause the end effector 106 to simultaneously sever and staple tissue clamped therein. The firing trigger 122 may be powered, require force from a user to engage, or some combination thereof. A manual firing release lever 126 can allow the firing system to be retracted before full firing travel has been completed, if desired, and, in addition, the firing release lever 126 can allow a surgeon, or other clinician, to retract the firing system in the event that the firing system binds and/or fails.

Additional details on the surgical stapling and severing device 100 and other surgical stapling and severing devices suitable for use with the present disclosure are described, for example, in U.S. Pat. No. 9,332,984 and in U.S. Patent Publication No. 2009/0090763, the disclosures of which are incorporated herein by reference in their entireties. Further, the surgical stapling and severing device need not include a handle, but instead can have a housing that is configured to couple to a surgical robot, for example, as described in U.S. Patent Publication No. 2019/0059889, the disclosure of which is incorporated herein by reference in its entirety.

As further shown in FIG. 1, a staple cartridge 200 can be utilized with the instrument 100. In use, the staple cartridge 200 is placed within and coupled to the elongate channel 104. While the staple cartridge 200 can have a variety of configurations, in this illustrated example, the staple cartridge 200, which is shown in more detail in FIGS. 2A-2B, has a proximal end 202a and a distal end 202b with a cartridge longitudinal axis (LC) extending therebetween. As a result, when the staple cartridge 200 is inserted into the elongate channel 104 (FIG. 1), the longitudinal axis (LC) is substantially or approximately parallel with the longitudinal axis (LS) of the elongate shaft 108. Further, the staple cartridge 200 includes a longitudinal slot 210 defined by two opposing walls 210a, 210b and configured to receive at least a portion of a firing member of a firing assembly, like firing assembly 400 in FIG. 4, as discussed further below. As shown, the longitudinal slot 210 extends from the proximal end 202a toward the distal end 202b of the staple cartridge 200. It is also contemplated herein that in other examples, the longitudinal slot 210 can be omitted.

The illustrated staple cartridge 200 includes staple cavities 212, 214 defined therein, in which each staple cavity 212, 214 is configured to removably house at least a portion of a staple (not shown). The number, shape, and position of the staple cavities can vary and can depend at least on the size and shape (e.g., mouth-like shape) of the staples to be removably disposed therein. In this illustrated example, the staple cavities are arranged in two sets of three longitudinal rows, in which the first set of staple cavities 212 is positioned on a first side of the longitudinal slot 210 and the second set of staple cavities 214 is positioned on a second side of the longitudinal slot 210. On each side of the longitudinal slot 210, and thus for each set of rows, a first longitudinal row of staple cavities 212a, 214a extends alongside the longitudinal slot 210, a second row of staple cavities 212b, 214b extends alongside the first row of staple cavities 212a, 214a, and a third row of staple cavities 212c, 214c extends alongside the second row of staple cavities 212b, 214b. Each row may be approximately parallel and the staple cavities that make up the rows may be approximately parallel in orientation with the longitudinal slot 210. As shown in FIGS. 2A, each staple cavity 212, 214 may include a maximum length SL of about 0.122 inches to about 0.124 inches and a maximum width SW of about 0.023 inches to about 0.027 inches. In addition, at least the centers of two adjacent cavities 212, 214 are spaced apart by about 0.158 inches.

Figure 3:
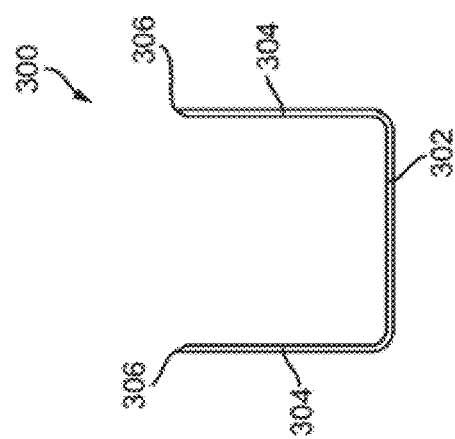
FIG. 3 is a side view of a staple in an unfired (pre-deployed) configuration that can be disposed within the staple cartridge of the surgical cartridge assembly of FIG. 2A.

The staples releasably stored in the staple cavities 212, 214 can have a variety of configurations. An exemplary staple 300 that can be releasably stored in each of the staple cavities 212, 214 is illustrated in FIG. 3 in its unfired (pre-deployed, unformed) configuration. The illustrated staple 300 includes a crown (base) 302 and two legs 304 extending from each end of the crown 302. In this example, the crown 302 extends in a linear direction and the staple legs 304 have the same unformed height. Further, prior to the staples 300 being deployed, the staple crowns 302 can be supported by staple drivers that are positioned within the staple cartridge 200 and, concurrently, the staple legs 304 can be at least partially contained within the staple cavities 212, 214. Further, the staple legs 304 can extend beyond a top surface, like top surface 206, of the staple cartridge 200 when the staples 300 are in their unfired positions. In certain instances, as shown in FIG. 3, the tips 306 of the staple legs 304 can be pointed and sharp which can incise and penetrate tissue.

In use, staples 300 can be deformed from an unfired position into a fired position such that the staple legs 304 move through the staple cavities 212, 214, penetrate tissue positioned between the anvil 102 and the staple cartridge 200, and contact the anvil 102. As the staple legs 304 are deformed against the anvil 102, the legs 304 of each staple 300 can capture a portion of the tissue within each staple 300 and apply a compressive force to the tissue. Further, the legs 304 of each staple 300 can be deformed downwardly toward the crown 302 of the staple 300 to form a staple entrapment area in which the tissue can be captured therein. In various instances, the staple entrapment area can be defined between the inner surfaces of the deformed legs and the inner surface of the crown of the staple. The size of the entrapment area for a staple can depend on several factors such as the length of the legs, the diameter of the legs, the width of the crown, and/or the extent in which the legs are deformed, for example.

In some examples, all of the staples disposed within the staple cartridge 200 can have the same unfired (pre-deployed, unformed) configuration. In other examples, the staples can include at least two groups of staples each having a different unfired (pre-deployed, unformed) configuration, e.g., varying in height and/or shape, relative to one another, etc.

Referring back to FIGS. 2A-2B, the staple cartridge 200 extends from a top surface or deck surface 206 to a bottom surface 208, in which the top surface 206 is configured as a tissue-facing surface and the bottom surface 208 is configured as a channel-facing surface. As a result, when the staple cartridge 200 is inserted into the elongate channel 104, as shown in FIG. 1, the top surface 206 faces the anvil 102 and the bottom surface 208 (obstructed) faces the elongate channel 104.

Figure 4:
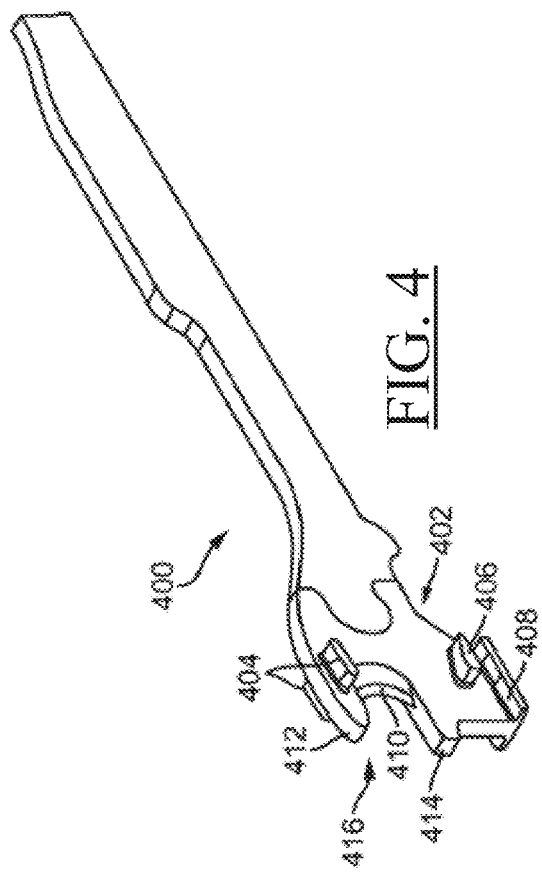
FIG. 4 is a perspective view of a knife and firing bar ("E-beam") of the surgical stapling and severing instrument of FIG. 1.
Figure 5:
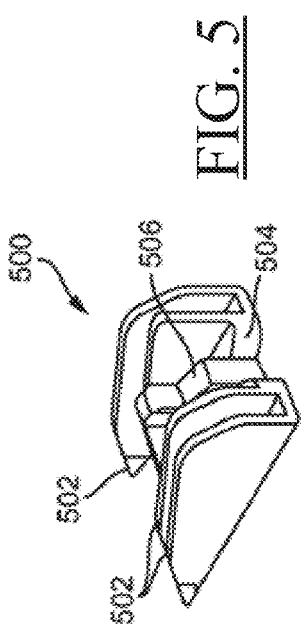
FIG. 5 is a perspective view of a wedge sled of a staple cartridge of the surgical stapling and severing instrument of FIG. 1.

With reference to FIGS. 4 and 5, a firing assembly such as, for example, firing assembly 400, can be utilized with a surgical stapling and severing device, like device 100 in FIG. 1. The firing assembly 400 can be configured to advance a wedge sled 500 having wedges 502 configured to deploy staples from the staple cartridge 200 into tissue captured between an anvil, like anvil 102 in FIG. 1, and a staple cartridge, like staple cartridge 200 in FIG. 1. Furthermore, an E-beam 402 at a distal portion of the firing assembly 400 may fire the staples from the staple cartridge. During firing, the E-beam 402 can also cause the anvil to pivot towards the staple cartridge, and thus move the end effector from the open position towards a closed position. The illustrated E-beam 402 includes a pair of top pins 404, a pair of middle pins 406, which may follow a portion 504 of the wedge sled 500, and a bottom pin or foot 408. The E-beam 402 can also include a sharp cutting edge 410 configured to sever the captured tissue as the firing assembly 400 is advanced distally, and thus towards the distal end of the staple cartridge. In addition, integrally formed and proximally projecting top guide 412 and middle guide 414 bracketing each vertical end of the cutting edge 410 may further define a tissue staging area 416 assisting in guiding tissue to the sharp cutting edge 410 prior to being severed. The middle guide 414 may also serve to engage and fire the staples within the staple cartridge by abutting a stepped central member 506 of the wedge sled 500 that effects staple formation by the end effector 106.

In use, the anvil 102 in FIG. 1 can be moved into a closed position by depressing the closure trigger in FIG. 1 to advance the E-beam 402 in FIG. 4. The anvil 102 can position tissue against at least the top surface 206 of the staple cartridge 200 in FIGS. 2A-2B. Once the anvil has been suitably positioned, the staples 300 in FIG. 3 disposed within the staple cartridge can be deployed.

To deploy staples from the staple cartridge, as discussed above, the sled 500 in FIG. 5 can be moved from the proximal end toward a distal end of the cartridge body, and thus, of the staple cartridge. As the firing assembly 400 in FIG. 4 is advanced, the sled can contact and lift staple drivers within the staple cartridge upwardly within the staple cavities 212, 214. In at least one example, the sled and the staple drivers can each include one or more ramps, or inclined surfaces, which can co-operate to move the staple drivers upwardly from their unfired positions. As the staple drivers are lifted upwardly within their respective staple cavities, the staples are advanced upwardly such that the staples emerge from their staple cavities and penetrate into tissue. In various instances, the sled can move several staples upwardly at the same time as part of a firing sequence.

As indicated above, the stapling device can be used in combination with a compressible adjunct. A person skilled in the art will appreciate that, while adjuncts are shown and described below, the adjuncts disclosed herein can be used with other surgical instruments and need not be coupled to a staple cartridge as described. Further, a person skilled in the art will also appreciate that the staple cartridges need not be replaceable.

As discussed above, with some surgical staplers, a surgeon is often required to select the appropriate staples having the appropriate staple height for tissue to be stapled. For example, a surgeon will utilize tall staples for use with thick tissue and short staples for use with thin tissue. In some instances, however, the tissue being stapled does not have a consistent thickness and thus, the staples cannot achieve the desired fired configuration for every section of the stapled tissue (e.g., thick and thin tissue sections). The inconsistent thickness of tissue can lead to undesirable leakage and/or tearing of tissue at the staple site when staples with the same or substantially greater height are used, particularly when the staple site is exposed to intra-pressures at the staple site and/or along the staple line.

Accordingly, various examples of adjuncts are provided that can be configured to compensate for varying thickness of tissue that is captured within fired (deployed) staples to avoid the need to take into account staple height when stapling tissue during surgery. That is, the adjuncts described herein can allow a set of staples with the same or similar heights to be used in stapling tissue of varying thickness (e.g., from thin to thick tissue) while also, in combination with the adjunct, providing adequate tissue compression within and between fired staples. Thus, the adjuncts described herein can maintain suitable compression against thin or thick tissue stapled thereto to thereby minimize leakage and/or tearing of tissue at the staple sites. In addition, exemplary adjuncts described herein may be configured to be absorbed in the body over a period of 100 to 300 days depending on implanted location and tissue health.

Alternatively, or in addition, the adjuncts can be configured to promote tissue ingrowth. In various instances, it is desirable to promote the ingrowth of tissue into an implantable adjunct, to promote the healing of the treated tissue (e.g., stapled and/or incised tissue), and/or to accelerate the patient's recovery. More specifically, the ingrowth of tissue into an implantable adjunct may reduce the incidence, extent, and/or duration of inflammation at the surgical site. Tissue ingrowth into and/or around the implantable adjunct may, for example, manage the spread of infections at the surgical site. The ingrowth of blood vessels, especially white blood cells, for example, into and/or around the implantable adjunct may fight infections in and/or around the implantable adjunct and the adjacent tissue. Tissue ingrowth may also encourage the acceptance of foreign matter (e.g., the implantable adjunct and the staples) by the patient's body and may reduce the likelihood of the patient's body rejecting the foreign matter. Rejection of foreign matter may cause infection and/or inflammation at the surgical site.

In general, the adjuncts provided herein are designed and positioned atop a staple cartridge, like staple cartridge 200. When the staples are fired (deployed) from the cartridge, the staples penetrate through the adjunct and into tissue. As the legs of the staple are deformed against the anvil that is positioned opposite the staple cartridge, the deformed legs capture a portion of the adjunct and a portion of the tissue within each staple. That is, when the staples are fired into tissue, at least a portion of the adjunct becomes positioned between the tissue and the fired staple. While the adjuncts described herein can be configured to be attached to a staple cartridge, it is also contemplated herein that the adjuncts can be configured to mate with other instrument components, such as an anvil of a surgical stapler. A person of ordinary skill will appreciate that the adjuncts provided herein can be used with replaceable cartridges or staple reloads that are not cartridge based.

In various embodiments, the adjunct or bioabsorbable materials disclosed herein can be comprised of an absorbable polymer. In certain embodiments, an adjunct can be comprised of foam, film, fibrous woven, fibrous non-woven polyurethane, polyether urethane, polyester urethane, polyester urea, polyester, polycarbonate, polyorthoester, polyanhydride, polyesteramide, polyphosphazenes, polyphosphoesters, polysaccharides, and/or polyoxaester. In other embodiments, an adjunct can be a copolymer including, for example, PGA (polyglycolic acid), PGA/PCL (poly(glycolic acid-co-caprolactone)), PLA/PCL (poly(lactic acid-co-polycaprolactone)), PLLA/PCL, PGA/TMC (poly(glycolic acid-co-trimethylene carbonate)), PDS, PEPBO, and the like. In various embodiments, an adjunct can include an organic material such as, for example, carboxymethyl cellulose, sodium alginate, hyaluronic acid, and/or oxidized regenerated cellulose. In various embodiments, an adjunct has a durometer in the 3-7 Shore A (30-50 Shore OO) ranges with a maximum stiffness of 15 Shore A (65 Shore OO). In certain embodiments, an adjunct can undergo 40% compression under 3 lbf load, 60% compression under 6 lbf load, and/or 80% compression under 20 lbf load, for example. In certain embodiments, one or more gasses, such as air, nitrogen, carbon dioxide, and/or oxygen, for example, can be bubbled through and/or contained within the adjunct.

Methods of Stapling Tissue

FIGS. 6A-6B illustrate an exemplary example of a stapling assembly 600 that includes a staple cartridge 200 and an adjunct 604. For sake of simplicity, the adjunct 604 is generally illustrated in FIGS. 6A-6B, and various configurations of the adjunct are described in more detail below. As shown, the adjunct 604 is positioned against the staple cartridge 200. While partially obstructed in FIGS. 6A-6B, the staple cartridge 200 includes staples 300, that are configured to be deployed into tissue. The staples 300 can have any suitable unformed (pre-deployed) height.

In the illustrated example, the adjunct 604 can be mated to at least a portion of the top surface or deck surface 206 of the staple cartridge 602. In some examples, the top surface 206 of the staple cartridge 200 can include one or more surface features which can be configured to engage the adjunct 604 to avoid undesirable movements of the adjunct 604 relative to the staple cartridge 200 and/or to prevent premature release of the adjunct 604 from the staple cartridge 200. Exemplary surface features are described further below and in U.S. Pat. No. 10,052,104, which is incorporated by reference herein in its entirety.

FIG. 6B shows the stapling assembly 600 placed within and coupled to the elongate channel 610 of surgical end effector 106. The anvil 102 is pivotally coupled to the elongate channel 610 and is thus moveable between open and closed positions relative to the elongate channel 610, and thus the staple cartridge 200. The anvil 102 is shown in a closed position in FIG. 6B and illustrates a tissue gap $T_{G1}$ created between the staple cartridge 602 and the anvil 612. More specifically, the tissue gap $T_{G1}$ is defined by the distance between the tissue-compression surface 102a of the anvil 102 (e.g., the tissue-engaging surface between staple forming pockets in the anvil) and the tissue-contacting surface 604a of the adjunct 604. In this illustrated example, both the tissue-compression surface 102a of the anvil 102 and the tissue-contacting surface 604a of the adjunct 604 is planar, or substantially planar (e.g., planar within manufacturing tolerances). As a result, when the anvil 102 is in a closed position, as shown in FIG. 6B, the tissue gap $T_{G1}$ is generally uniform (e.g., nominally identical within manufacturing tolerances) when no tissue is disposed therein. In other words, the tissue gap $T_{G1}$ is generally constant (e.g., constant within manufacturing tolerances) across the end effector 106 (e.g., in the y-direction). In other examples, the tissue-compression surface of the anvil can include a stepped surface having longitudinal steps between adjacent longitudinal portions, and thus create a stepped profile (e.g., in the y-direction). In such examples, the tissue gap $T_{G1}$ can be varied.

The adjunct 604 is compressible to permit the adjunct to compress to varying heights to thereby compensate for different tissue thickness that are captured within a deployed staple. The adjunct 604 has an uncompressed (undeformed), or pre-deployed, height and is configured to deform to one of a plurality of compressed (deformed), or deployed, heights. For example, the adjunct 604 can have an uncompressed height which is greater than the fired height of the staples 300 disposed within the staple cartridge 200 (e.g., the height (H) of the fired staple 300a in FIG. 7A). That is, the adjunct 604 can have an undeformed state in which a maximum height of the adjunct 604 is greater than a maximum height of a fired staple (e.g., a staple that is in a formed configuration).

In use, once the surgical stapling and severing device, like device 100 in FIG. 1, is directed to the surgical site, tissue is positioned between the anvil 102 and the stapling assembly 600 such that the anvil 102 is positioned adjacent to a first side of the tissue and the stapling assembly 600 is positioned adjacent to a second side of the tissue (e.g., the tissue can be positioned against the tissue-contacting surface 604a of the adjunct 604). Once tissue is positioned between the anvil 102 and the stapling assembly 600, the surgical stapler can be actuated, e.g., as discussed above, to thereby clamp the tissue between the anvil 102 and the stapling assembly 600 (e.g., between the tissue-compression surface 102a of the anvil 102 and the tissue-contacting surface 604a of the adjunct 604) and to deploy staples from the cartridge through the adjunct and into the tissue to staple and attach the adjunct to the tissue.

As shown in FIG. 7A, when the staples 300 are fired, tissue (T) and a portion of the adjunct 604 are captured by the fired (formed) staples 300a. The fired staples 300a each define the entrapment area therein, as discussed above, for accommodating the captured adjunct 604 and tissue (T). The entrapment area defined by a fired staple 300a is limited, at least in part, by a height (H) of the fired staple 300a.

Referring to FIG. 7B, the adjunct 604 may have pores 632 with a median pore size of about 0.025 mm$^3$ to about 0.300 mm$^3$, such as about 0.022 mm$^3$. In some examples, the adjunct 604 may have one or more struts 634 between the pore 632 that provide support and strength to the adjunct 604. In particular, the adjunct 604 may include a plurality of struts 634, having a median strut thickness ST of about 0.025 mm to about 0.300 mm, such as about 0.08 mm.

Figure 8:
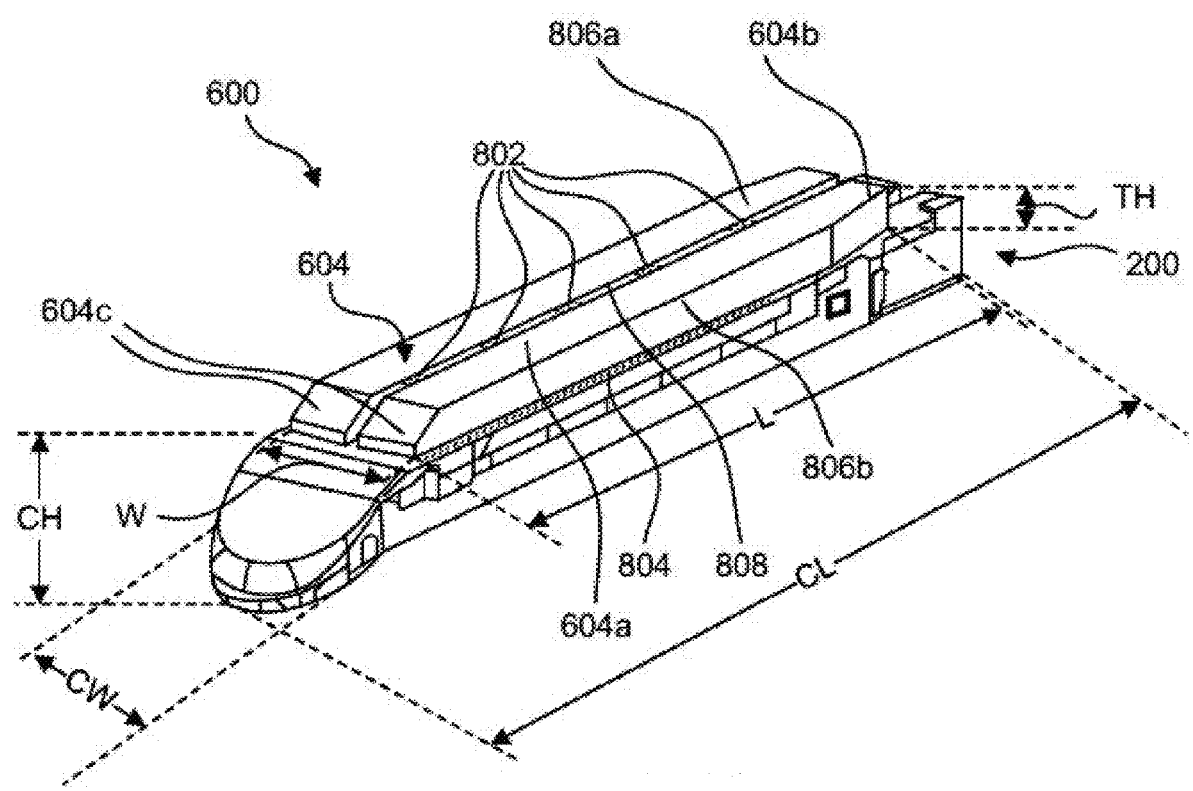
FIG. 8 is a perspective view of an exemplary cartridge assembly.

FIG. 8 illustrates a perspective view of a staple cartridge assembly 600 with an adjunct 604 and a staple cartridge 200. The adjunct 604 has a tissue contacting surface 604a, a proximal end 604c, and a distal end 604b. The adjunct 604 may include a slot/slit 808 separating or partially separating two parallel portions of the adjunct 604. In one example, adjunct 604 may include a slot 808 separating two parallel portions of the adjunct 604, while in another example, adjunct 604 may include a slit 808 separating two parallel portions of the adjunct 604 and also one or more bridges (e.g., five bridges) 802 connecting the two parallel portions of the adjunct 604. At least one bridge has a length in the longitudinal direction of about 0.035 inches to about 0.046 inches. The adjunct 604 has a length L of about 40 mm to about 80 mm, such as about 60 mm to about 65 mm, about 66.04 mm to about 66.3 mm, about 45 mm to about 55 mm, or about 51.12 mm to about 51.38 mm. The adjunct 604 has a width W of about 8 mm to about 12 mm, such as about 9.75 mm to about 10.25 mm or about 10.025 mm to about 10.035 mm. The adjunct 604 may also have a thickness or height TH of about 2.5 mm to about 3.5 mm, such as about 2.85 mm to about 3.15 mm or about 2.95 mm to about 3.05 mm.

The cartridge 200 has a height CH of about 6.3 mm to about 8.1 mm, a width CW of about 8.9 mm to about 14 mm, and a length CL of about 80 mm to about 90 mm such as about 86.7 mm.

The staple cartridge 200 may include one or more raised ledges 804 along one or more sides of the adjunct 604 to help align the adjunct 604 on the deck of the staple cartridge 200. Although not shown in FIG. 8, the staple cartridge 200 may also include an adhesive or buttress adhesive material to attach the adjunct 604. The adjunct 604 may be attached to the cartridge 200 with about 100 mg to about 120 mg of the adhesive or buttress adhesive material.

Adjusting Mechanical Properties Through Stimuli-Responsive Materials

The strength required to retain staples, sutures, screws, and the like, may conflict with the requirements for endoscopic deployment. As described above, the end effector 106 (shown in FIG. 1) comprising the cartridge 200 and adjunct 604 is closed or substantially closed for inserting through a trocar to the delivery site. As the implant strength increases (for maintaining staples and the hemostatic seal), there is an increased force required to compress the implant for insertion through the trocar. Therefore, the surgical adjunct 604 needs to have adjustable mechanical properties such that the material is sufficiently compressible during delivery through the trocar but increases strength at the delivery site to retain staples, sutures, and screws and maintain a hemostatic seal during the recovery period.

As described herein, the surgical adjunct 604 can be tuned for the particular purpose before, during, and after surgical procedures and have one or more of the functional groups described below that modulate the mechanical properties. In particular, the adjunct 604 described has one or more stimuli-responsive functional groups that respond to certain stimulus either ex vivo or in vivo, such that the compressibility of the adjunct 604 can be modulated during delivery and after firing.

FIG. 9A is a side view of the end effector 106 in a delivery configuration, where the adjunct 604 is compressible between the anvil 102 and the cartridge 200. As illustrated, the end effector 106 can include a staple cartridge 200 and an adjunct 604 that is bioabsorbable can include a shape-memory polymer 624 that is compressible in a delivery configuration. In certain embodiments, the adjunct 604 is releasably retained on the cartridge 200. As illustrated in FIG. 9A, when the end effector 106 closes around tissue T, the adjunct 604 can compress from a thickness of the uncompressed adjunct UT to a thickness of compressed adjunct CT in response to a variation in tissue thickness.

FIG. 9B is a side view of the end effector 106 after firing of staples 300, where the adjunct 604 is no longer compressed between the anvil 102 and the cartridge 200. As shown, the adjunct 604 is released from the cartridge 200 after firing. The adjunct 604 is shown to maintain the thickness of the compressed adjunct CT and the thickness of uncompressed adjunct UT from pre-firing in FIG. 9A.

In some embodiments, the adjunct 604 can undergo a change in mechanical properties before firing of staples such that the uncompressed portion CT and compressed portion CT will be maintained after firing and releasing adjunct 604 and tissue T. In other embodiments, the adjunct 604 can undergo a change in mechanical properties after firing and within a predetermined time period. In such an example, the uncompressed portion CT and compressed portion CT can either expand or contract in response to the staple height and the tissue thickness as the tissue heals. As would be appreciated by those of skill in the art, a change in mechanical properties of the adjunct 604 can be advantageous to ensure a hemostatic seal during changes in tissue inflammatory responses and throughout the healing process.

To control mechanical properties of the bioabsorbable material, the adjunct 604 includes shape-memory polymer 624 that can swell via reversible transformations from linear polymer systems 625 to non-linear polymer systems 626, as shown in FIGS. 9C and 9D. Stimuli-responsive functional groups can allow for transitions from linear polymer systems to complex architectures such as star, cyclic, or hyperbranched systems. The transition between linear polymers 625 to non-linear polymers 626 can include bonding among adjacent functional groups along the same polymer strand, as shown by the dashed lines in FIGS. 9C and 9D. Alternatively, or in addition thereto, the bonding can be cross-linking among functional groups along adjacent polymer strands, as shown by the dotted lines between the primary strand of FIG. 9C and a secondary strand in FIG. 9D (secondary polymer strand is not illustrated in FIG. 9C for clarity). The shape-memory polymer may include a backbone including one or more polymers selected from polyurethane, polyether urethane, polyester urethane, polyester urea, polyester, polycarbonate, polyorthoester, polyanhydride, polyesteramide, polyphosphazenes, polyphosphoesters, polysaccharides, and/or polyoxaester.

As would be understood by one of skill in the art, the polymer backbone may be further functionalized after formation of the backbone. For instance, a polyurethane backbone can be synthesized via a reaction between an isocyanate and a polyol. After formation of the polyurethane backbone, additional functional groups may be added. Alternatively, or in addition thereto, the polymer backbone precursors can be previously functionalized with one or more functional groups. As a non-limiting example of such a case, an isocyanate functionalized with one functional group may react with a polyol functionalized with a second functional group such that the polyurethane backbone is formed with pendant functional groups in the same step.

In certain embodiments, the shape-memory polymer 624 can be configured to adjust mechanical properties either through physical expansion (swelling) or a material phase change. The mechanical properties, such as the compression strength (compressing the polymer), tensile strength (stretching the polymer), flexural strength (bending of the polymer), torsional strength (twisting of the polymer), impact strength (under the effects of direct hammering or firing), tear resistance, ultimate elongation, and/or Young's modulus (ratio of stress to strain), can be configured to increase after releasing the shape-memory polymer 624 from the staple cartridge 200. The functional groups can undergo reversible bonding with adjacent functional groups via stimulation comprising at least one of heat, light, water, electrical, magnetic, electromagnetic, ultrasound, pH, and the like. As would be appreciated by one of skill in the relevant art, each functional group can be selective to transition upon only one type of stimulation or may be able to transition with a combination of stimuli.

The mechanical properties can be reversed when using dampening implants, for instance, when using an adjunct 604 that needs to be sutured in vivo. To prevent damage during implant manipulation and suturing procedures, the shape-memory polymer 624 can be configured to have increased mechanical properties, but can be specifically tailored to retain a rubbery state (to prevent tearing) upon exposure to biological conditions (increased temperatures, pH, and the like).

In some embodiments, the shape-memory polymer 624 can be programmed via temperature, such that the adjunct 604 is deformed by a maximum change in compression ($e_{max}$) with a constant loading rate (e.g., 0.01 s$^{-1}$) at a programming temperature ($T_P$) and subsequently cooled to a loading temperature ($T_L$) while holding at the $e_{max}$. Outside of potential relaxation ($\Delta e$), the strain is recovered once raised to the recovery temperature ($T_R$). In general, the adjunct 604 may be designed such that the glass transition temperature ($T_g$) is between $T_L$ and $T_R$. In addition, the adjunct 604 may also be designed such that the transition occurs through effective plasticization or degradation such that the effective $T_g$ depresses and allows for recovery with a liquid emersion step prior to deployment. Liquid emersion may be water or any in vivo fluids within the body at the delivery site.

In certain other embodiments, the shape-memory polymer 624 can be designed around light mediation such that bonds of the functional groups are created or broken upon exposure to differing wavelengths of light. Activation or deactivation of the bonds within these systems can be done with a transmittable wavelength through the tissue or within the endoscopic procedure.

Temperature-triggered architectural transformations can be achieved in the present system through the use of thermally labile functional groups. Example thermally labile functional groups include Diels-Alder adducts and/or azo groups. For instance, Diels-Alder linkages based on a furan-maleimide reaction can be formed at relatively low temperatures ranging from about room temperature (~25° C.) to about 60° C. The furan-maleimide reaction can be reversed at higher temperatures, such as equal to or greater than approximately 90° C. The retro-cycloaddition of the furan-maleimide reaction generates free furan and maleimide moieties. In general, for the Diels-Alder thermal transition, the increase in mechanical properties of the adjunct 604 can occur in the range of about 34° C. to about 60° C. such as in the range of about 34° C. to about 40° C.

In some embodiments, to achieve a change in mechanical properties under a Diels-Alder reaction, the backbone of the shape-memory polymer 624 can include a diene and a dienophile moiety. The diene and a dienophile moiety can be incorporated in the polymer's monomer backbone or as pendent groups.

In some examples, the shape-memory polymer 624 can include a suitable diene, such as substituted or unsubstituted alkene. In some embodiments, the suitable diene can include, without limitation, furans, thiophenes, or pyrroles. Without intending to be bound, some example dienes include, without limitation, substituted or unsubstituted 1,2- propadiene, isoprene, 1,3-butadiene, 2,4-octanedione, 1,5-cyclooctadiene, norbornadiene, 2-pyrone, dicyclopentadiene, 1H-pyrrole-2-carboxylic acid, 1H-pyrrole-3-carboxylic acid, 3,5-dimethyl-1H-pyrrole-2-carboxylic acid, 1,5-dimethyl-1H-pyrrole-2-carboxylic acid, 2,4,5-trimethyl-1H-pyrrole-3-carboxylic acid, 5-phenyl-1H-pyrrole-2-carboxylic acid, 2,4-dimethyl-1H-pyrrole-3-carboxylic acid, 2,5-dimethyl-1H-pyrrole-3-carboxylic acid, 3-methyl-1H-pyrrole-2-carboxylic acid, 5-(3,4-dimethylphenyl)-2-methyl-1H-pyrrole-3-carboxylic acid, 1-methyl-1H-pyrrole-2-carboxylic acid, 2-methyl-1H-pyrrole-3-carboxylic acid, furan-2-carboxylic acid, furan-3-carboxylic acid, 2-(furan-2-yl) acetic acid, 3-(5-methylfuran-2-yl) propanoic acid, 5-ethylfuran-2-carboxylic acid, 5-isobutyl-2-methylfuran-3-carboxylic acid, 4,5-dimethylfuran-2-carboxylic acid, thiophene-2-carboxylic acid, 4,5-dimethylthiophene-2-carboxylic acid, 3-methylthiophene-2-carboxylic acid, 5-methylthiophene-2-carboxylic acid, 5-phenylthiophene-2-carboxylic acid, 2-(thiophen-2-yl) acetic acid, thiophene-3-carboxylic acid, 2-(thiophen-3-yl) acetic acid, 5-ethylthiophene-2-carboxylic acid, and 5-methyl-4-phenylthiophene-3-carboxylic acid.

In some embodiments, the diene undergoes the Diels-Alder cycloaddition reaction with a suitable dienophile that can include either a substituted or unsubstituted alkene or alkyne. In some embodiments, a suitable dienophile can include, without limitation, substituted or unsubstituted maleimide, acrolein, methyl vinyl ketone, acrylic acid, methyl acrylate, acrylamide, acrylonitrile, methyl acrylate, dimethyl maleate, dimethyl fumarate, maleic anhydride, Maleonitrile, butenolide, alpha-methylene gamma-butolactone, N-methylmaleimide, N-ethylmaleimide, dimethyl acetylene dicarboxylate, 6-maleimidohexanoic acid, 2-butenal, 2-Maleimidoacetic acid, 3-Maleimidopropionic acid, 3-Maleimidobenzoic acid, 3-(2,5-Dioxopyrrol-1-yl) hexanoic acid, 4-Maleimidobutyric acid, 4-Maleimidobenzoic acid, 4-(2,5-Dioxopyrrol-1-yl) hexanoic acid, 4-(2,5-dioxo-2,5-dihydro-pyrrol-1-yl)-benzoic acid, 5-Maleimidopentanoic acid, 6-Maleimidohexanoic acid, 6-(3-methyl-2,5-dioxopyrrol-1-yl) hexanoic acid, 6-(2,5-dioxopyrrol-1-yl)-2-methylhexanoic acid, 6-(2,5-Dioxopyrrol-1-yl)-4-methylhexanoic acid, 7-(2,5-Dioxo-2,5-dihydro-1H-pyrrol-1-yl) heptanoic acid, 9-(2,5-dioxopyrrol-1-yl) nonanoic acid, 10-(2,5-dioxopyrrol-1-yl) decanoic acid, 11-Maleimidoundecanoic acid, 13-(2,5-Dioxo-2,5-dihydro-1H-pyrrol-1-yl)tridecanoic acid, N-(Carboxyheptyl) maleimide, N-(4-Carboxy-3-hydroxyphenyl) maleimide, and α-Maleimidyl-ω-Carboxyl Poly(ethylene glycol).

In some embodiments, to achieve a change in mechanical properties under a thermal trigger, the backbone of the shape-memory polymer 624 can include an azo moiety. The azo moiety can be incorporated in the polymer's monomer backbone or as pendent groups. In general, for an azo thermal transition, the increase in mechanical properties of the adjunct 604 can occur in the range of about 60° C. to about 110° C. Alternatively, or in addition thereto, the azo moiety can be cleaved under light stimulation when the azo compound includes a substituted or unsubstituted aryl or heteroaryl groups within the azo molecule. Photoresponsive behaviors of the azo moiety within the shape-memory polymer 624 can be selected based on the azo compound. For example, an azo moiety with a trans-cis isomerization may be responsive to different wavelengths. For illustrative purposes, an azo moiety may experience photoresponsiveness in the trans-isomer at a wavelength ranging from about 350 nm to about 370 nm, whereas the cis-isomer may experience photoresponsiveness at a wavelength ranging from about 430 nm to about 460 nm. As would be appreciated by one of skill in the art, a shape-memory polymer containing one or more azo moieties may be tuned for a specific wavelength and/or temperature trigger.

In some examples, the shape-memory polymer 624 can include a suitable monozo, disazo, trisazo, polyazo, or azoic moiety. The monoazo moieties can be schematically represented by the formula Z—N=N—W, where Z and W are substituted or unsubstituted aryl or heterocyclic groups. Diazo moieties contain two —N=N— groups and can be symmetric or asymmetric. Polyazo moieties are characterized by the repetition of the azo group from three or more times in the same molecule. Suitable azo moieties can include, without limitation, substituted or unsubstituted triazolinediones, poly(vinylcarbazole), 1,1'-Azobis(cyclohexanecarbonitrile) or ACHN, 4,4'-azobis(4-cyanovaleric acid), azobenzene, 4,4-dihydroxyazobenzene, p-azobenzenearsonate, 2,2'-azobis(2-amidinopropane) dihydrochloride, 4,4'-azobis(4-cyanopentanoic acid), azobisisobutyronitrile, azodicarbonamide, azoxy compounds, para-azoxyanisole, azoxybenzene, balsalazide, 3-Hydroxy-4-[(2-hydroxy-5-methylphenyl) azo]-1-naphthalenesulfonic acid ("calmagite"), diethyl azodicarboxylate, diimide, diisopropyl azodicarboxylate, 4,4'-dinitro-3,3'-diazenofuroxan, 1,3-diphenyltriazene, disodium 4,4'-dinitrostilbene-2,2'-disulfonate, fazadinium bromide, 4H-1,2,4-triazole-3,4,5-triamine with 5,5'-(1,2-diazenediyl)bis[2H-tetrazole] ("G2ZT"), glycoazodyes, methylazoxymethanol, methylazoxymethanol acetate, olsalazine (also known under trade name "Dipentum"), phenazopyridine, 3-phenylazoacetylacetone, 7,18-bis(4-phenyldiazenylphenyl)-7,18-diazaheptacyclo[14.6.2.22,5.03,12.04,9.013,23.020,24] hexacosa-1(23),2,4,9,11,13,15,20 (24),21,25-decaene-6,8,17,19-tetrone ("pigment red 178"), potassium azodicarboxylate, 4-[(E)-{4-formyl-5-hydroxy-6-methyl-3-[(phosphonooxy)methyl] pyridin-2-yl}diazenyl] benzene-1,3-disulfonic acid ("PPADS"), 6-methyl-2-(phenylazo)-3-pyridinol ("SIB-1757"), 4-phenyldiazenylphenol ("solvent yellow 7"), sulfasalazine, tetramethylazodicarboxamide, disodium 3-hydroxy-4-[(2-arsonophenyl)diazenyl] naphthalene-2,7-disulfonate ("thorin"), and 1,3,5-tri (p-glycosyloxyphenyl azo)-2,4,6-trihydroxybenzene ("Yariv reagent").

In some embodiments, to achieve a change in mechanical properties under photo-stimulation, the backbone of the shape-memory polymer 624 can include a styrylpyrene moiety. The styrylpyrene moiety can be incorporated in the polymer's monomer backbone or as pendent groups. Photoresponsive behaviors of the styrylpyrene moiety within the shape-memory polymer 624 can be selected to tune the wavelength of light required to initiate the change in mechanical properties. For instance, the shape-memory polymer 624 having a styrylpyrene moiety can be configured to undergo reversible transition of mechanical properties upon exposure to a wavelength of light ranging from about 310 nm to about 450 nm.

In some examples, the shape-memory polymer 624 can include a suitable styrylpyrene moiety. Suitable styrylpyrene moieties can include, without limitation, substituted or unsubstituted 1-styrylpyrene, phenanthracene, 3,4-benzopyrene, 1,2:5,6-dibenzanthracene, 1,2-benzanthracene, 7,12-dimethylbenzanthracene ("DMBA"), 1-[(1R,2S,4R)-5,6-dimethyl-2-bicyclo[2.2.1] heptanyl] pyrene, 1-(2-phenylethenyl) acenaphthylene, 2-(2-phenylethyl) dibenzofuran, 3-(2-phenylsulfanylethyl)-2-thia-3-azatricyclo[6.3.1.04,12] dodeca-1(11),4,6,8(12),9-pentaene, 1-(2-phenylethynyl) phenanthrene, 4-(2-phenylethenyl) pyrene, 2-(pyridin-2-ylmethoxy)-1,10-phenanthroline, 1-(3- phenylpropyl) imidazo[2,1-b][1,3] benzothiazole, trimethyl-(4-pyren-1-ylphenyl) silane, 1-methyl-2-methylidene-6-(1-methylnaphthalen-2-yl)-3-prop-2-enyl-3,3a-dihydro-1H-acenaphthylene, and the like.

In some embodiments, to achieve a change in mechanical properties under photo-stimulation, the backbone of the shape-memory polymer 624 can include an ortho-nitrobenzyl moiety. The ortho-nitrobenzyl moiety can be incorporated in the polymer's monomer backbone or as pendent groups. In general, the shape-memory polymer 624 having an ortho-nitrobenzyl moiety is configured to reversibly transition upon exposure to a wavelength of light ranging from about 310 nm to about 440 nm.

In some examples, the shape-memory polymer 624 can include a suitable ortho-nitrobenzyl moiety. Suitable ortho-nitrobenzyl moieties can include, without limitation, substituted or unsubstituted [4-[(2-nitrophenyl)methyl]phenyl] methanediol, 1-(4,5-dimethoxy-2-nitro-phenyl)-but-3-ene-1-ol, 4-((1-(4,5-dimethoxy-2-nitrophenyl) but-3-en-1-yl) oxy)-4-oxobutanoic acid, 3-((acryloyloxymethyl-2-hydroxymethyl) propionyloxy)methyl-2-nitrobenzyl, 4-cyano-4-(phenylcarbonothioylthio) pentanoate ("ANCP"), 2-nitrobenzyl cyclohexylcarbamate, 2-[(2-nitrobenzyl)oxy]-1H-isoindole-1,3 (2H)-dione, 2-[(2-Nitrophenyl)methyl-thio]-1,3-benzoxazole, 2-(2-Methyl-5-nitroimidazol-1-yl) ethyl thiophene-2-carboxylate, (E)-3-(2-chlorophenyl)-N-cyclopentyl-2-propenamide, (2E)-N-(5-chloropyridin-2-yl)-3-(2-methoxyphenyl) acrylamide, N-[(2-nitrophenyl) methylideneamino] thiophene-2-carboxamide, N-cyclohexyl-3-(2-methoxyphenyl) prop-2-enamide, (2E)-N-cyclo heptyl-3-(2-nitrophenyl) prop-2-enamide, 2-(2-nitrophenyl)-N-(thiophen-2-ylmethyl) acetamide, N-(3,5-dichloro-4-methylpyridin-2-yl)-2-(1-oxidopyridin-1-ium-2-yl) sulfanylacetamide, 1-(2-Nitrophenyl)-3-phenyl-2-thiourea, N-bicyclo[2.2.1] hept-2-yl-2-(2-nitrophenyl) acetamide, 2-[2-(2-Chloroanilino)-2-oxoethyl] sulfanylbenzoic acid, N-(2,5-dimethylphenyl)-3-methyl-1-oxo-3,4-dihydro-1H-isochromene-3-carboxamide, [(2-nitrophenyl) amino]-N-(1,3,4-thiadiazol-2-yl) carboxamide, 2-cyano-N-(2-methylcyclohexyl)-3-(5-methylthiophen-2-yl) prop-2-enamide, (E)-2-cyano-N-(2-methylcyclohexyl)-3-(3-methylthiophen-2-yl) prop-2-enamide, (E)-1-(2-nitrophenyl)-N-phenylmethoxymethanimine, N-(2-nitrophenyl)-N'-pyridin-2-ylurea, 2-(2,4-dimethyl-6-nitrophenoxy)-N-(5-methyl-1,2-oxazol-3-yl) propanamide, 2-(2-Nitrophenoxy)-1-(2-phenylpyrrolidin-1-yl) ethanone, 4-Chloro-1-[2-(4-methoxyphenoxy)ethylsulfanyl]-2-nitrobenzene, 2-[2-Oxo-2-(thiophen-2-ylmethylamino)ethyl] sulfanylbenzoic acid, 1-(2-nitrophenyl)-N-phenyl-methoxymethanimine, N-(2-chloropyridin-3-yl)-2-[(2-nitrothien-3-yl)thio] acetamide, 2-(2-Nitrothiophen-3-yl) sulfanyl-1-pyrrolidin-1-ylethanone, (2-nitrophenyl)methyl N-[1-(2-hydroxyethoxy)-5-methylhexan-3-yl] carbamate, and the like.

In some embodiments, to achieve a change in mechanical properties, the backbone of the shape-memory polymer 624 can be a coumarin moiety. The coumarin moiety can be incorporated in the polymer's monomer backbone or as pendent groups. Coumarin moieties undergo a reversible [2πs+2πs] cycloaddition reaction upon irradiation with specific wavelengths in the UV region, which is applied to impart intrinsic healability, shape-memory, and reversible properties into polymers. During photoirradiation, four different types of coumarin dimers are formed: anti head-to-head, anti head-to-tail, syn head-to-head, and syn head-to-tail.

In some examples, the shape-memory polymer 624 can include a suitable coumarin or coumarin-derivative moiety including dihydrofurano coumarins, furano coumarins, pyrano coumarins, phenyl coumarins, and bicoumarins. Suitable coumarin and/or coumarin-derivative moieties can include, without limitation, substituted or unsubstituted 2H-1-benzopyran-2-one ("coumarin"), 2-(Dimethylamino) ethyl methacrylate (DMAEMA) 7-(2-methacryloyloxy-ethoxy)-4-methylcoumarin (CMA), poly(DMAEMA-co-CMA). Dimethylaminoethyl acrylate (DMAEA), 6-Iodo-2H-chromen-2-one, 4-Hydroxycoumarin, 3-Hydroxycoumarin, 6-Methoxycoumarin, 4-Trimethylsi-loxycumarin, and the like. In some embodiments, the shape-memory polymer 624 may be functionalized with coumarinyl end groups such that a single polymer strand can undergo a photodimerization.

In some embodiments, to achieve a change in mechanical properties, the backbone of the shape-memory polymer 624 can be an anthracene moiety. The anthracene moiety can be incorporated in the polymer's monomer backbone or as pendent groups. In general, anthracene groups undergo [4+4] photo-dimerization when irradiated by UV light ($\lambda$>300 nm) and can be reversed to the original monomers via exposure to a higher energy UV light ($\lambda$<300 nm).

In some examples, the shape-memory polymer 624 can include a suitable anthracene or anthracene-derivative moiety. Suitable anthracene and/or anthracene-derivative moieties can include, without limitation, substituted or unsubstituted Benzo[a]pyrene, Phenothiazine, Anthranol, Dibenzothiophene 5-oxide, 1,4,5-Trimethylnaphthalene, 4-Methyldibenzothiophene, Pyrene, 10-Methylacridin-9 (10H)-one, gamma-Fagarine, 9-Hydroxymethyl-10-methyl-anthracene, 2-Dodecylphenanthrene, Phenanthrene, 2-dodecyl-9,10-dihydro-, 2-Octyltriphenylene, 8a-Methyl-3,5-dimethylidene-3a,4,4a,6,7,8,9,9a-octahydrobenzo[f][1] benzo furan-2-one, Furanoeremophilane, 4-[(E)-2-(1-naphthyl) vinyl] biphenyl, 1,7-diazatricyclo[7.3.0.03,7] dodeca-3,5,9,11-tetraene-2,8-dione ("Pyrocoll"), (3R,4aR,8aR)-5, 8a-dimethyl-3-prop-1-en-2-yl-2,3,4,4a, 7,8-hexahydro-1H-naphthalene ("alpha-Selinene"), 3,4-dihydro-2H-pyrimido [1,2-b][1,2] benzothiazole, and the like. In some embodiments, the shape-memory polymer 624 may be functionalized with anthracene end groups such that a single polymer strand can undergo a photodimerization.

In some embodiments, to achieve a change in mechanical properties, the backbone of the shape-memory polymer 624 can include a disulfide moiety. The disulfide moiety is a functional group with the formula R—S—S—R', where R and R' are either the same or different groups. The disulfide moiety can be incorporated in the polymer's monomer backbone or as pendent groups.

In general, disulfide moieties can be redox-responsive. Redox-active disulfide bonds are reversible and responsive to changes in the redox potential of the surrounding environment, and the formation or reduction of these disulfide bonds serve to increase the mechanical properties of the shape-memory polymer 624 after firing and delivery. The disulfide moieties can be intramolecular (oxidoreductases, allosteric disulfides, etc.) or mixed disulfides between a cysteine residue and a small-molecule thiol resulting in glutathionylated and cysteinylated adducts.

In some examples, the shape-memory polymer 624 can include a suitable disulfide moiety including, without limitation, substituted or unsubstituted diamines with disulfide groups, thiols with disulfide groups, or inimers with disulfide groups. Suitable disulfide moieties can include, without limitation, substituted or unsubstituted thioredoxin disulfide, 2-(2'-bromoisobutyryloxy)ethyl-2"-methacryloyloxyethyl disulfide, and the like.

In some embodiments, to achieve a change in mechanical properties, the backbone of the shape-memory polymer 624 can be a diselenide moiety. The diselenide moiety can be incorporated in the polymer's monomer backbone or as pendent groups.

In general, diselenide moieties can be redox-responsive. Selenolate-diselenide equilibria are the same as their sulfur-containing counterparts, thiolate-diselenide equilibria, and involve the reversible formation of diselenides from selenolates through the two-electron oxidation of the selenolate group.

In some examples, the shape-memory polymer 624 can include a suitable diselenide moiety including, without limitation, substituted or unsubstituted selenols, diselenides, selenides, selenoxides, selenoketones, selenones, selenenic acids, or seleninic acids. Suitable diselenide moieties can include, without limitation, substituted or unsubstituted diselenocarbonate. selenocysteamine, selenocystine, selenocystine, glutathione, oxidized glutathione, and selenocystamine, and the like.

In some embodiments, to achieve a change in mechanical properties, the backbone of the shape-memory polymer 624 can be at least one of a diene and a dienophile moiety, a styrylpyrene moiety, an azo moiety, an ortho-nitrobenzyl moiety, a coumarin moiety, an anthracene moiety, a disulfide moiety, a diselenide moiety, or combinations thereof.

In general, these molecular changes via bond formation and breaking can be tailored to allow a macroscopic geometric change in the shape-memory polymer 624. The transformation of the shape-memory polymer 624 can be thermal, photo, redox, or mechano-responsive.

In some embodiments, the functional groups along the shape-memory polymer 624 are more highly concentrated along a portion of the adjunct 604 so as to form a gradient of compression strength along a portion of the porous body 634. In general, the adjunct 604 may have a compression strength of about 30 kPa to about 70 kPa, such as about 30 kPa to about 60 kPa (e.g., about 42 kPa), about 30 kPa to about 50 kPa, about 32.5 kPa to about 37.5 kPa. In some embodiments, the adjunct 604 may have a compression strength of about 15 to about 50 kPa in the second zone during delivery and a compression strength of about 30 kPa to about 70 kPa after delivery through the trocar, but before firing of staples. In order to test compression strengths, an adjunct 604 was placed in a humid warm environment at approximately 37° C., compressed to a first height, then a second height shorter than the first height, and then released back to the first height at which point the adjunct's compression strength was measured.

In any of the embodiments described herein, the adjunct 604 can be configured to reversible transition between an approximately linear polymer and an approximately non-linear polymer within approximately 0.01 seconds to approximately 15 minutes such that the swelling of the shape-memory polymer 624 occurs between the time of deployment through the trocar and firing of the staples, including various surgical procedure time delays. In some cases, the stimulation may cause the reversible transition to occur much faster, such that the shape-memory polymer 624 reaches substantial swelling and compression strength within seconds of being delivered through the trocar (e.g., within approximately 1 second, 2 seconds, 3 seconds, 4 seconds, 5 seconds, 10 seconds, 15 seconds, 20 seconds, 30 seconds, and any time in between). In other embodiments, the shape-memory polymer 624 may be configured to reach substantial swelling and compression strength within a delayed time period from exposure to stimulation (e.g., after approximately 30 seconds, after 45 seconds, after 1 minute, after 2 minutes, and any time in between).

In some embodiments, the adjunct 604 may have a lower compressive strength during delivery and the compressive strength or other mechanical properties only increase after exposure to stimulus after deployment. Alternatively, the adjunct 604 can be compressed to a small thickness having high compressive strength but better margins for delivery through a trocar.

In some examples, the adjunct 604 may have a tensile strength of about 30 kPa to about 90 kPa such as about 45 kPa to about 85 kPa or about 55 kPa to about 75 kPa during delivery. After delivery, the adjunct 604 may increase the tensile strength from about 30 to about 45 kPa, or from about 45 kPa to about 65 kPa, or from about 55 kPa to about 75 kPa after exposure to stimulus. In some examples, the adjunct 604 will have tensile strength of about 110 kPa to about 150 kPa during delivery, that can increase upon exposure to a stimulus to a range of about 140 kPa to about 220 kPa.

Figure 10A:
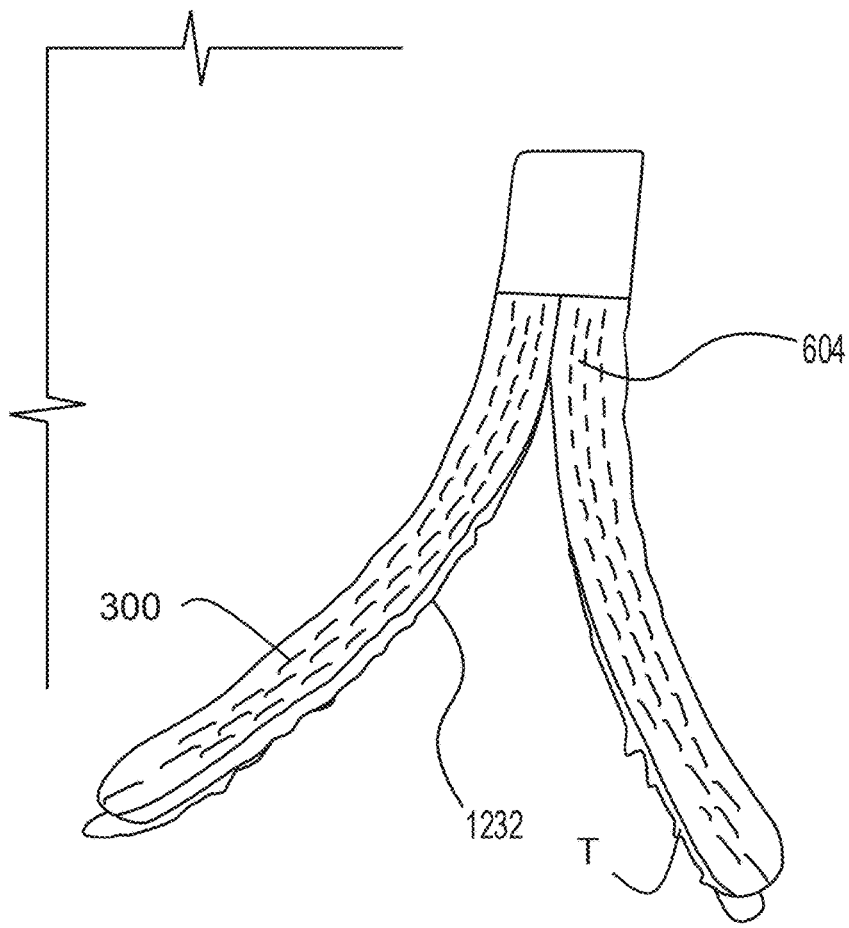
FIG. 10A is a top perspective view of an exemplary adjunct after use.
Figure 10B:
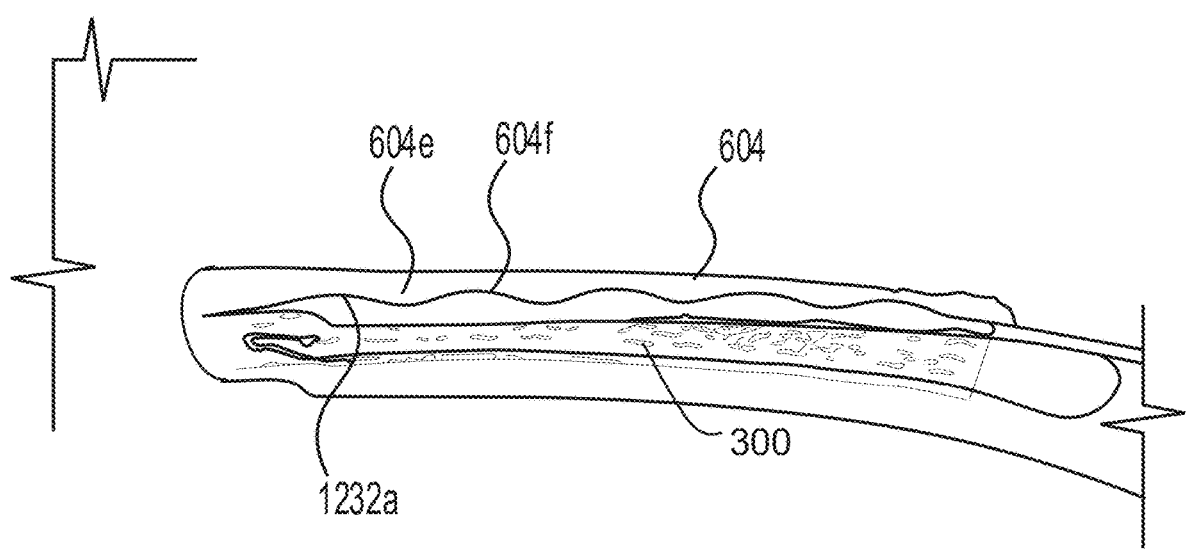
FIG. 10B is a side view of an exemplary adjunct after use.

FIGS. 10A and 10B show top and side view of an adjunct 604 after firing staples 300 and cutting tissue T. As shown, adjunct 604 may split in two post firing. Where the adjunct 604 contacts with the tissue T, bumps 604e, 604f may form that correspond to the texture and thickness variation in the tissue. This means that adjunct 604 can adapt to different heights and compressions depending on the application.

Figure 11:
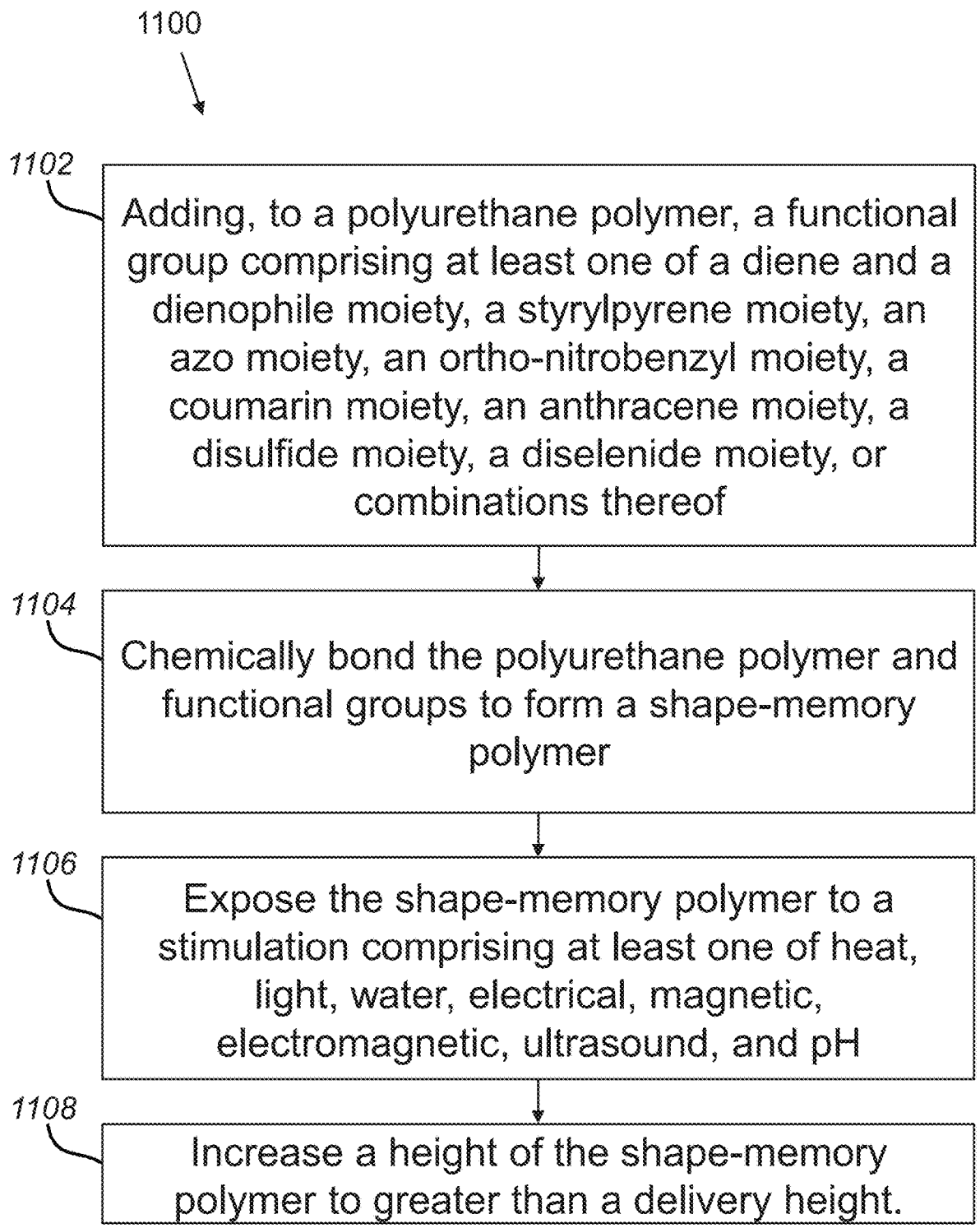
FIG. 11 is a flow chart showing an exemplary method of forming a surgical adjunct with spatial control of mechanical properties in bioabsorbable material.

FIG. 11 is a flowchart of a method 1100 for forming a surgical adjunct 604, including a bioabsorbable material that itself includes a shape-memory polymer. The techniques for adjusting mechanical properties described herein may offer an added benefit of increasing adjunct strength and durability in combination with positive in vivo interactions (e.g., biocompatibility, wound healing, tissue integration, chemotherapy, anti-inflammatory, bone growth and integration, ligament and tendon repair, etc.) when the adjunct is delivered to the tissue site, as described herein. As such, the techniques described herein may allow the bioabsorbable material itself to aid in the healing process of the surrounding tissue. In addition, the embedding techniques described herein may offer an added benefit of preventing fibrous encapsulation of the foam cushion, and/or providing tunable release profiles for a variety of medical additives delivered to the tissue site.

Specifically with respect to FIG. 11, method 1100 used for forming a bioabsorbable material (e.g., a foam) having shape-memory polymer may include adding, to a polyurethane polymer, a functional group that can reversibly cross-link upon exposure to stimulation (step 1102). The functional group can be at least one of a diene and a dienophile moiety, a styrylpyrene moiety, an azo moiety, an ortho-nitrobenzyl moiety, a coumarin moiety, an anthracene moiety, a disulfide moiety, a diselenide moiety, or combinations thereof. Method 1100 can next include chemically bonding the polyurethane polymer and functional groups to form the shape-memory polymer (step 1104). In some examples, the bioabsorbable material may include a polyurethane, or alternatively, may include polyether urethane, polyester urethane, polyester urea, polyester, polycarbonate, polyorthoester, polyanhydride, polyesteramide, polyphosphazenes, polyphosphoesters, polysaccharides, and/or polyoxaester. Method 1100 also includes exposing the shape-memory polymer to a stimulation comprising at least one of heat, light, water, electrical, magnetic, electromagnetic, ultrasound, and pH (step 1106). After exposure to the stimulation, method 1100 includes increasing a height of the shape-memory polymer to greater than a delivery height (step 1108). Method 1100 can end after step 1108 or can optionally include adding a medical additive to the porous body. In such examples, the medical additives may include medicants to treat pain and/or promote wound healing, tissue growth, infection reduction, and the like.

As will be appreciated by one skilled in the art, The embodiments described above are cited by way of example, and the present invention is not limited by what has been particularly shown and described hereinabove. Rather, the scope of the invention includes both combinations and sub combinations of the various features described hereinabove, as well as variations and modifications thereof which would occur to persons skilled in the art upon reading the foregoing description and which are not disclosed in the prior art.

In some examples, disclosed devices (e.g., end effector, surgical adjunct, and/or staple cartridges) and methods involving one or more disclosed devices may involve one or more of the following clauses:

Clause 1: A bioabsorbable material configured to be delivered to tissue, the material comprising: a shape-memory polymer compressible in a delivery configuration and configured to swell within a predetermined period of time; wherein the shape-memory polymer comprises one or more functional groups for reversible bonding between adjacent functional groups to transition between an approximately linear polymer and an approximately non-linear polymer upon exposure to a stimulation.

Clause 2: The bioabsorbable material of clause 1, wherein the shape-memory polymer transitions from the delivery configuration to a swollen configuration when exposed to a temperature in a range of about 34° C. to about 40° C.

Clause 3: The bioabsorbable material of clause 1, wherein the stimulation comprises at least one of heat, light, water, electrical, magnetic, electromagnetic, ultrasound, and pH.

Clause 4: The bioabsorbable material of clause 1, wherein the shape-memory polymer comprises a reaction product of a polyol and an isocyanate.

Clause 5: The bioabsorbable material of clause 1, wherein the functional groups comprise a diene and a dienophile moieties, and wherein the shape-memory polymer is configured to reversibly transition upon exposure to a temperature in a range of about 34° C. to about 40° C.

Clause 6: The bioabsorbable material of clause 1, wherein the functional groups comprise a styrylpyrene moiety, and wherein the shape-memory polymer is configured to reversibly transition upon exposure to a wavelength of light ranging from about 310 nm to about 450 nm.

Clause 7: The bioabsorbable material of clause 1, wherein the functional groups comprise an azo moiety, and wherein the shape-memory polymer is configured to reversibly transition upon exposure to a temperature above about 60° C.

Clause 8: The bioabsorbable material of clause 1, wherein the functional groups comprise an ortho-nitrobenzyl moiety, and wherein the shape-memory polymer is configured to reversibly transition upon exposure to a wavelength of light ranging from about 310 nm to about 440 nm.

Clause 9: The bioabsorbable material of clause 1, wherein the functional groups comprise a coumarin moiety, and wherein the shape-memory polymer is configured to reversibly transition to a first compression strength upon exposure to a wavelength of light ranging from about 200 nm to about 260 nm; and wherein the shape-memory polymer is configured to reversibly transition to a second compression strength upon exposure to a wavelength of light ranging from about 350 nm to about 560 nm.

Clause 10: The bioabsorbable material of clause 1, wherein the functional groups comprise an anthracene moiety, and wherein the shape-memory polymer is configured to reversibly transition to the approximately non-linear configuration upon exposure to a wavelength of light greater than about 300 nm, and transition to the approximately linear configuration upon exposure to a wavelength of light less than about 300 nm.

Clause 11: The bioabsorbable material of clause 5, wherein the functional groups comprise at least one of a disulfide moiety and a diselenide moiety, and wherein the shape-memory polymer is configured to reversibly transition upon exposure to at least one of a change in temperature, a change in pH, a reactive oxygen species, or combinations thereof.

Clause 12: The bioabsorbable material of clause 1, wherein the predetermined period of time ranges from approximately 0.01 seconds to approximately 120 seconds.

Clause 13: The bioabsorbable material of clause 2, wherein the bioabsorbable material has a compression strength of about 50 kPa to about 90 kPa in the delivery configuration, and a compression strength of about 30 kPa to about 70 kPa in the swollen configuration.

Clause 14: The bioabsorbable material of clause 1, wherein the bioabsorbable material degrades according to a degradation profile in response to exposure to a fluid comprising at least one of a predetermined temperature, an enzyme-catalyst, and a predetermined pH.

Clause 15: The bioabsorbable material of clause 1, further comprising one or more medical additives configured to remain chemically bonded to the shape-memory polymer.

Clause 16: The bioabsorbable material of clause 15, wherein the one or more medical additives are further configured to be released to or approximate the tissue.

Clause 17: A bioabsorbable material configured to be delivered to tissue, the material comprising: a shape-memory polymer compressible in a delivery configuration and configured to swell within a predetermined period of time upon exposure to a stimulation, the shape-memory polymer comprising a polyurethane backbone and one or more functional groups for reversible bonding between adjacent functional groups to transition between an approximately linear polymer to an approximately non-linear polymer.

Clause 18: The bioabsorbable material of clause 17, wherein the stimulation comprises at least one of heat, light, water, electrical, magnetic, electromagnetic, ultrasound, and pH.

Clause 19: The bioabsorbable material of clause 1, wherein the predetermined period of time ranges from approximately 0.01 seconds to approximately 120 seconds.

Clause 20: The bioabsorbable material of clause 17, wherein the one or more functional groups comprise at least one of a diene and a dienophile moiety, a styrylpyrene moiety, an azo moiety, an ortho-nitrobenzyl moiety, a coumarin moiety, an anthracene moiety, a disulfide moiety, a diselenide moiety, or combinations thereof.

Clause 21: A method to form a bioabsorbable material configured to be placed inside a body of a human, the method comprising the steps of: adding, to a polyurethane polymer, a functional group comprising at least one of a diene and a dienophile moiety, a styrylpyrene moiety, an azo moiety, an ortho-nitrobenzyl moiety, a coumarin moiety, an anthracene moiety, a disulfide moiety, a diselenide moiety, or combinations thereof; and chemically bonding the polyurethane polymer and functional groups to form a shape-memory polymer.

Clause 22: The method of clause 21, further comprising the step of: exposing the shape-memory polymer to a stimulation comprising at least one of heat, light, water, electrical, magnetic, electromagnetic, ultrasound, and pH.

Clause 23: The method of clause 22, wherein the shape-memory polymer is configured to reversibly transition between an approximately linear polymer to an approximately non-linear polymer.

Clause 24: The method of clause 22, wherein the shape-memory polymer is compressible in a delivery configuration.

Clause 25: The method of clause 21, wherein the bioabsorbable material comprises a delivery height ranging from about 0.01 mm to about 1 mm when in the delivery configuration.

Clause 26: The method of clause 25, further comprising the step of: increasing a height of the shape-memory polymer to greater than the delivery height.

Clause 27: The method of clause 21, further comprising the step of: exposing the bioabsorbable material to a fluid comprising at least one of a predetermined temperature, an enzyme-catalyst, and a predetermined pH such that the bioabsorbable material degrades according to a degradation profile.

Clause 28: A bioabsorbable material configured to be delivered to tissue, the material comprising: a shape-memory polymer compressible in a delivery configuration and configured to swell within a predetermined period of time; wherein the shape-memory polymer comprises one or more functional groups for reversible bonding between adjacent functional groups to transition between an approximately linear polymer and an approximately non-linear polymer upon exposure to a stimulation.

Clause 29: The material of clause 28, wherein the shape-memory polymer transitions from the delivery configuration to a swollen configuration when exposed to a temperature in a range of about 34° C. to about 40° C.

Clause 30: The material of clauses 28 or 29, wherein the stimulation comprises at least one of heat, light, water, electrical, magnetic, electromagnetic, ultrasound, and pH.

Clause 31: The material any of clauses 28-30, wherein the shape-memory polymer comprises a reaction product of a polyol and an isocyanate.

Clause 32: The material of any of clauses 28-31, wherein the functional groups comprise a diene moiety and a dienophile moiety, and wherein the shape-memory polymer is configured to reversibly transition upon exposure to a temperature above in a range of about 34° C. to about 40° C.

Clause 33: The material of any of clauses 28-31, wherein the functional groups comprise a styrylpyrene moiety, and wherein the shape-memory polymer is configured to reversibly transition upon exposure to a wavelength of light ranging from about 310 nm to about 450 nm.

Clause 34: The material of any of clauses 28-31, wherein the functional groups comprise an azo moiety, and wherein the shape-memory polymer is configured to reversibly transition upon exposure to a temperature above about 60° C.

Clause 35: The material of any of clauses 28-31, wherein the functional groups comprise an ortho-nitrobenzyl moiety, and wherein the shape-memory polymer is configured to reversibly transition upon exposure to a wavelength of light ranging from about 310 nm to about 440 nm.

Clause 36: The material of any of clauses 28-31, wherein the functional groups comprise a coumarin moiety, wherein the shape-memory polymer is configured to reversibly transition to a first compression strength upon exposure to a wavelength of light ranging from about 200 nm to about 260 nm; and wherein the shape-memory polymer is configured to reversibly transition to a second compression strength upon exposure to a wavelength of light ranging from about 350 nm to about 560 nm.

Clause 37: The material of any of clauses 28-31, wherein the functional groups comprise an anthracene moiety, and wherein the shape-memory polymer is configured to reversibly transition to the approximately non-linear configuration upon exposure to a wavelength of light greater than about 300 nm, and transition to the approximately linear configuration upon exposure to a wavelength of light less than about 300 nm.

Clause 38: The material any of any of clauses 28-31, wherein the functional groups comprise at least one of a disulfide moiety and a diselenide moiety, and wherein the shape-memory polymer is configured to reversibly transition upon exposure to at least one of a change in temperature, a change in pH, a reactive oxygen species, or combinations thereof.

Clause 39: The material of any of clauses 28-38, wherein the predetermined period of time ranges from approximately 0.028 seconds to approximately 120 seconds.

Clause 40: The material of clauses 28 or 29, wherein the bioabsorbable material has a compression strength of about 50 kPa to about 90 kPa in the delivery configuration, and a compression strength of about 30 kPa to about 70 kPa in the swollen configuration.

Clause 41: The material any of clauses 28-40, wherein the bioabsorbable material degrades according to a degradation profile in response to exposure to a fluid comprising at least one of a predetermined temperature, an enzyme-catalyst, and a predetermined pH.

Clause 42: The material of any of clauses 28-41, further comprising one or more medical additives configured to remain chemically bonded to the shape-memory polymer, wherein the one or more medical additives are further configured to be released to or approximate the tissue.

What is claimed is:

1. A bioabsorbable material configured to be delivered to tissue, the material comprising: a shape-memory polymer compressible in a delivery configuration and configured to swell for a predetermined period of time comprising a range from approximately 0.01 seconds to approximately 120 seconds; wherein the shape-memory polymer comprises one or more functional groups for reversible bonding between adjacent functional groups to transition between an approximately linear polymer and an approximately non-linear polymer upon exposure to a stimulation.

2. The bioabsorbable material of claim 1, wherein the shape-memory polymer transitions from the delivery configuration to a swollen configuration when exposed to a temperature in a range of about 34° C. to about 40° C.

3. The bioabsorbable material of claim 1, wherein the stimulation comprises at least one of heat, light, water, electrical, magnetic, electromagnetic, ultrasound, and pH.

4. The bioabsorbable material of claim 3, wherein the bioabsorbable material has a compression strength of about 50 kPa to about 90 kPa in the delivery configuration, and a compression strength of about 30 kPa to about 70 kPa in the swollen configuration.

5. The bioabsorbable material of claim 1, wherein the shape-memory polymer comprises a reaction product of a polyol and an isocyanate.

6. The bioabsorbable material of claim 1, wherein the functional groups comprise a diene and a dienophile moieties, and wherein the shape-memory polymer is configured to reversibly transition upon exposure to a temperature in a range of about 34° C. to about 40° C.

7. The bioabsorbable material of claim 6, wherein the functional groups comprise at least one of a disulfide moiety and a diselenide moiety, and wherein the shape-memory polymer is configured to reversibly transition upon exposure to at least one of a change in temperature, a change in pH, a reactive oxygen species, or combinations thereof.

8. The bioabsorbable material of claim 1, wherein the functional groups comprise a styrylpyrene moiety, and wherein the shape-memory polymer is configured to reversibly transition upon exposure to a wavelength of light ranging from about 310 nm to about 450 nm.

9. The bioabsorbable material of claim 1, wherein the functional groups comprise an azo moiety, and wherein the shape-memory polymer is configured to reversibly transition upon exposure to a temperature above about 60° C.

10. The bioabsorbable material of claim 1, wherein the functional groups comprise an ortho-nitrobenzyl moiety, and wherein the shape-memory polymer is configured to reversibly transition upon exposure to a wavelength of light ranging from about 310 nm to about 440 nm.

11. The bioabsorbable material of claim 1, wherein the functional groups comprise a coumarin moiety, wherein the shape-memory polymer is configured to reversibly transition to a first compression strength upon exposure to a wavelength of light ranging from about 200 nm to about 260 nm; and wherein the shape-memory polymer is configured to reversibly transition to a second compression strength upon exposure to a wavelength of light ranging from about 350 nm to about 560 nm.

12. The bioabsorbable material of claim 1, wherein the functional groups comprise an anthracene moiety, and wherein the shape-memory polymer is configured to reversibly transition to the approximately non-linear configuration upon exposure to a wavelength of light greater than about 300 nm, and transition to the approximately linear configuration upon exposure to a wavelength of light less than about 300 nm.

13. The bioabsorbable material of claim 1, wherein the bioabsorbable material degrades according to a degradation profile in response to exposure to a fluid comprising at least one of a predetermined temperature, an enzyme-catalyst, and a predetermined pH.

14. The bioabsorbable material of claim 1, further comprising one or more medical additives configured to remain chemically bonded to the shape-memory polymer.

15. The bioabsorbable material of claim 14, wherein the one or more medical additives are further configured to be released to or approximate the tissue.

16. A bioabsorbable material configured to be delivered to tissue, the material comprising: a shape-memory polymer compressible in a delivery configuration and configured to swell for a predetermined period of time upon exposure to a stimulation, wherein the predetermined period of time comprises a range from approximately 0.01 seconds to approximately 120 seconds, the shape-memory polymer comprising a polyurethane backbone and one or more functional groups for reversible bonding between adjacent functional groups to transition between an approximately linear polymer to an approximately non-linear polymer.

17. The bioabsorbable material of claim 16, wherein the stimulation comprises at least one of heat, light, water, electrical, magnetic, electromagnetic, ultrasound, and pH.

18. The bioabsorbable material of claim 16, wherein the one or more functional groups comprise at least one of a diene and a dienophile moiety, a styrylpyrene moiety, an azo moiety, an ortho-nitrobenzyl moiety, a coumarin moiety, an anthracene moiety, a disulfide moiety, a diselenide moiety, or combinations thereof.

19. A method to form a bioabsorbable material configured to be placed inside a body of a human, the method comprising the steps of: adding, to a polyurethane polymer, a functional group comprising at least one of a diene and a dienophile moiety, a styrylpyrene moiety, an azo moiety, an ortho-nitrobenzyl moiety, a coumarin moiety, an anthracene moiety, a disulfide moiety, a diselenide moiety, or combinations thereof; and chemically bonding the polyurethane polymer and functional groups to form a shape-memory polymer.

20. The method of claim 19, further comprising the step of: exposing the shape-memory polymer to a stimulation comprising at least one of heat, light, water, electrical, magnetic, electromagnetic, ultrasound, and pH.

21. The method of claim 20, wherein the shape-memory polymer is configured to reversibly transition between an approximately linear polymer to an approximately non-linear polymer.

22. The method of claim 20, wherein the shape-memory polymer is compressible in a delivery configuration.

23. The method of claim 19, wherein the bioabsorbable material comprises a delivery height ranging from about 0.01 mm to about 1 mm when in the delivery configuration.

24. The method of claim 23, further comprising the step of: increasing a height of the shape-memory polymer to greater than the delivery height.

25. The method of claim 19, further comprising the step of: exposing the bioabsorbable material to a fluid comprising at least one of a predetermined temperature, an enzyme-catalyst, and a predetermined pH such that the bioabsorbable material degrades according to a degradation profile.

* * * * *